United States Patent
Thakur et al.

(10) Patent No.: US 9,332,924 B2
(45) Date of Patent: May 10, 2016

(54) POSTURE DETECTION USING THORACIC IMPEDANCE

(75) Inventors: Pramodsingh Hirasingh Thakur, White Bear Lake, MN (US); Abhilash Patangay, Inver Grove Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1177 days.

(21) Appl. No.: 13/324,201

(22) Filed: Dec. 13, 2011

(65) Prior Publication Data

US 2012/0157874 A1   Jun. 21, 2012

Related U.S. Application Data

(60) Provisional application No. 61/423,128, filed on Dec. 15, 2010.

(51) Int. Cl.
  *A61B 5/053* (2006.01)
  *A61B 5/0205* (2006.01)
  (Continued)

(52) U.S. Cl.
  CPC .............. *A61B 5/0538* (2013.01); *A61B 5/0205* (2013.01); *A61B 5/1116* (2013.01); *A61B 5/6869* (2013.01); *A61B 5/103* (2013.01);
  (Continued)

(58) Field of Classification Search
  CPC .. A61B 5/0205; A61B 5/0538; A61B 5/1116; A61B 5/6869; A61B 5/103; A61B 5/686; A61B 2560/0462; A61N 1/36521; A61N 1/36535
  USPC ........................................................ 600/547
  See application file for complete search history.

(56) References Cited

U.S. PATENT DOCUMENTS 6,076,015 A   6/2000   Hartley et al.
7,440,803 B2  10/2008  Ni et al.
(Continued)

FOREIGN PATENT DOCUMENTS

EP   1911399 A1   4/2008
EP   2143467 A1   1/2010
(Continued)

OTHER PUBLICATIONS

"U.S. Appl. No. 13/324,174, Advisory Action mailed Aug. 6, 2013", 3 pgs.
(Continued)

*Primary Examiner* — Rene Towa
(74) *Attorney, Agent, or Firm* — Schwegman Lundberg & Woessner, P.A.

(57) ABSTRACT

Physiological data, such as thoracic impedance data, can be obtained over a first time window to establish a baseline, or can be used to form one or more data clusters. Additional physiological data, such as thoracic impedance test data acquired over a later time window, can be obtained and compared to the baseline or data clusters to determine an indication of worsening heart failure. In an example, a quantitative attribute of one or more data clusters can be monitored and used to provide an indication of worsening heart failure. A posture discrimination metric can be obtained, such as using the physiological data obtained over the first time window. The additional physiological data, such as can be obtained over a second time window, can be compared to the posture discrimination metric to provide a patient posture status.

20 Claims, 13 Drawing Sheets

(51) Int. Cl.
*A61B 5/11* (2006.01)
*A61B 5/00* (2006.01)
A61B 5/103 (2006.01)
A61N 1/365 (2006.01)

(52) U.S. Cl.
CPC ......... *A61B5/686* (2013.01); *A61B 2560/0462* (2013.01); *A61N 1/36521* (2013.01); *A61N 1/36535* (2013.01)

(56) References Cited

U.S. PATENT DOCUMENTS

| | | |
|---|---|---|
| 7,559,901 B2 | 7/2009 | Maile et al. |
| 7,603,170 B2 | 10/2009 | Maplewood et al. |
| 7,640,056 B2 | 12/2009 | Belalcazar |
| 7,764,996 B2 | 7/2010 | Zhang et al. |
| 7,787,946 B2 | 8/2010 | Stahman |
| 7,805,185 B2 | 9/2010 | Zhang et al. |
| 7,805,196 B2 | 9/2010 | Miesel et al. |
| 8,821,404 B2 | 9/2014 | Thakur et al. |
| 2006/0271121 A1 | 11/2006 | Ding et al. |
| 2007/0282185 A1 | 12/2007 | Belalcazar |
| 2008/0091114 A1 | 4/2008 | Min et al. |
| 2008/0300504 A1 | 12/2008 | Lefkov et al. |
| 2009/0275846 A1 | 11/2009 | Costa Ribalta et al. |
| 2009/0318815 A1 | 12/2009 | Barnes et al. |
| 2010/0004712 A1 | 1/2010 | Zhao et al. |
| 2010/0030292 A1 | 2/2010 | Sarkar et al. |
| 2010/0113961 A1 | 5/2010 | Ohlander et al. |
| 2010/0249756 A1 | 9/2010 | Koh |
| 2010/0256462 A1 | 10/2010 | Rappaport et al. |

FOREIGN PATENT DOCUMENTS

| | | |
|---|---|---|
| JP | 2008514258 A | 5/2008 |
| JP | 2010524636 A | 7/2010 |
| JP | 2014501135 A | 1/2014 |
| WO | WO-2007001219 A1 | 1/2007 |
| WO | WO-2008014078 A2 | 1/2008 |
| WO | WO-2008137166 A1 | 11/2008 |
| WO | WO-2012082698 A3 | 6/2012 |

OTHER PUBLICATIONS

"U.S. Appl. No. 13/324,174, Examiner Interview Summary mailed Apr. 17, 2013", 3 pgs.

"U.S. Appl. No. 13/324,174, Final Office Action mailed May 30, 2013", 17 pgs.

"U.S. Appl. No. 13/324,174, Non Final Office Action mailed Jan. 2, 2013", 20 pgs.

"U.S. Appl. No. 13/324,174, Non Final Office Action mailed Dec. 17, 2013", 17 pgs.

"U.S. Appl. No. 13/324,174, Notice of Allowance mailed Apr. 29, 2014", 5 pgs.

"U.S. Appl. No. 13/324,174, Response filed Apr. 7, 2014 to Non Final Office Action mailed Dec. 17, 2013", 13 pgs.

"U.S. Appl. No. 13/324,174, Response filed Apr. 23, 2013 to Non Final Office Action mailed Jan. 2, 2013", 20 pgs.

"U.S. Appl. No. 13/324,174, Response filed Jul. 29, 2013 to Final Office Action mailed May 30, 2013", 15 pgs.

"U.S. Appl. No. 13/324,174, Response filed Aug. 28, 2013 to Final Office Action mailed May 30, 2013", 15 pgs.

"Chinese Application Serial No. 201180066597.4, Office Action mailed Apr. 22, 2015", With English Translation, 19 pgs.

"Chinese Application Serial No. 201180066597.4, Office Action mailed Aug. 22, 2014", With English Translation, 11 pgs.

"International Application Serial No. PCT/US2011/064560, International Preliminary Report on Patentability mailed Jun. 27, 2013", 8 pgs.

"Japanese Application Serial No. 2013-544678, Office Action mailed Apr. 15, 2014", With English Translation, 8 pgs.

POSTURE DETECTION USING THORACIC IMPEDANCE

CLAIM OF PRIORITY

This application claims the benefit of priority under 35 U.S.C. §119(e) of Thakur et al., U.S. Provisional Patent Application Ser. No. 61/423,128, entitled "POSTURE DETECTION USING THORACIC IMPEDANCE", filed on Dec. 15, 2010, which is herein incorporated by reference in its entirety.

BACKGROUND

Cardiac rhythm management devices can include implantable or other ambulatory devices, such as pacemakers, cardioverter-defibrillators, cardiac resynchronization therapy (CRT) devices, or devices that can monitor one or more physiological parameters, or provide one or a combination of pacing, defibrillation, or cardiac resynchronization therapies, or that can both monitor one or more physiological parameters and provide therapy. In an example, such devices can be configured for use with a plurality of implanted or external electrodes, such as to detect or treat cardiac, respiratory, or other conditions. Information obtained, such as using the electrodes, can be used to provide a diagnosis or predict an impending disease state, or to initiate or adjust therapy.

Early detection of physiological conditions that can indicate heart failure ("HF," sometimes referred to as congestive heart failure, "CHF"), such as before a patient experiences cardiac decompensation associated with such heart failure, can help to indicate treatment that may prevent cardiac decompensation from occurring. Zhao et al., in U.S. Patent Publication No. 2010/0004712, entitled SYSTEMS AND METHODS FOR USE BY AN IMPLANTABLE MEDICAL DEVICE FOR DETECTING HEART FAILURE BASED ON THE INDEPENDENT INFORMATION CONTENT OF IMMITANCE VECTORS, refers to detecting heart failure based on independent informational content of a plurality of immittance vectors, and controlling a function based on the amount of independent informational content. (See Zhao et al. at paragraph [0008].)

Accurate and efficient posture detection can help to provide important information to a clinician or a cardiac rhythm management device, such as to ensure accurate interpretation of one or more physiological parameters, or to determine a therapy. Maile et al., in U.S. Pat. No. 7,559,901, entitled DETERMINING A PATIENT'S POSTURE FROM MECHANICAL VIBRATIONS OF THE HEART, refers to determining a patient's posture by monitoring heart sounds. (See Maile et al. at the Abstract.)

Overview

Various electrical or mechanical functions of the heart can provide a variety of physiological parameters that can indicate the onset of a condition, for instance, heart failure, arrhythmia (fibrillation, tachycardia, bradycardia), ischemia, or the like. These physiological parameters can include, for example, heart sounds (e.g., S3 amplitude), DC impedance near the lungs, heart rate, respiration rate, weight, or intracardiac pressure. Further examples of a physiological parameter can include, but are not limited to, a hormone level, a blood count, a neural activity, a muscle activity, or any other physiological parameter. At least some of these parameters can indicate the onset or change of a condition, which can be used to provide an alert that therapy (or therapy adjustment) is needed, such as defibrillation, change in pacing, or the like. It can be difficult, however, to determine whether an event is beginning when only some measurements for these parameters indicate the onset of a condition.

This document describes, among other things, systems, methods, machine-readable media, or other techniques that can involve obtaining physiological data, sorting the physiological data into one or more data clusters or establishing a baseline, obtaining additional test data, and comparing the test data to the data clusters or baseline to determine an indication of heart decompensation.

The techniques can involve obtaining physiological data over a first time window to establish a baseline that can include two or more discrete groups, wherein one or more groups can correspond to a patient posture. Additional physiological data can be obtained and compared to the groups to provide a present patient posture status.

The techniques described and illustrated herein can be directed toward diagnosing a patient risk for cardiac decompensation in advance of heart failure. Also, several techniques of posture detection are presented. The techniques described and illustrated herein can also or alternatively be used to determine or distinguish among one or more of pulmonary edema, pleural edema, or peripheral edema.

The present techniques can provide one or more cardiac decompensation indicators that can provide enhanced specificity, such as over other approaches using only raw impedance data to predict cardiac decompensation. Impedance data can modulate in response to normal neurohormonal or circadian variations in a patient. Therefore, trends in impedance data can be difficult to discern. Also, global changes in patient fluid levels can affect all measured impedance vectors at once, which can confound decompensation detection based solely on raw thoracic impedance data used to determine fluid accumulation. By contrast, the present techniques can include, among other things, comparing at least two impedance vectors, such as during one or more time windows that can include at least one postural change. In such an approach, the effects due to global fluid level changes can be minimized. This can help provide a better indication of an increased risk for heart failure decompensation.

The present inventors have recognized, among other things, that a problem to be solved can include providing more sensitive or more specific advance notification of a patient's risk for imminent cardiac decompensation. In an example, the present subject matter can provide a solution to this problem, such as by obtaining physiological data, forming a function of first physiological data and second physiological data, identifying one or more trends in the physiological data, and providing advance notification of a patient's risk for cardiac decompensation using the trend information.

The present inventors have recognized, among other things, that another problem to be solved can include providing a patient posture status, such as using physiological data readily available to an implantable cardiac rhythm management device—such as without requiring a dedicated 3-axis accelerometer, tilt-switch, or other sensor for detecting patient orientation or posture. In an example, the present subject matter can provide a solution to this problem, such as by establishing a posture discrimination comparison metric using one or more thoracic impedance measurements, obtaining thoracic impedance test data, and providing a posture status by comparing the thoracic impedance test data to the posture discrimination comparison metric.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes can represent different instances of similar components. The drawings illustrate generally, by way of example, but not by way of limitation, various embodiments discussed in the present document.

DETAILED DESCRIPTION

Physiological data, such as thoracic impedance data, can be obtained over a first time window to establish a baseline, or can be used to form one or more data clusters. Additional physiological data, such as thoracic impedance test data acquired over a later time window, can be obtained and compared to the baseline or data clusters to determine an indication of worsening heart failure. In an example, a quantitative attribute of one or more data clusters can be monitored and used to provide an indication of worsening heart failure.

Figure 1:
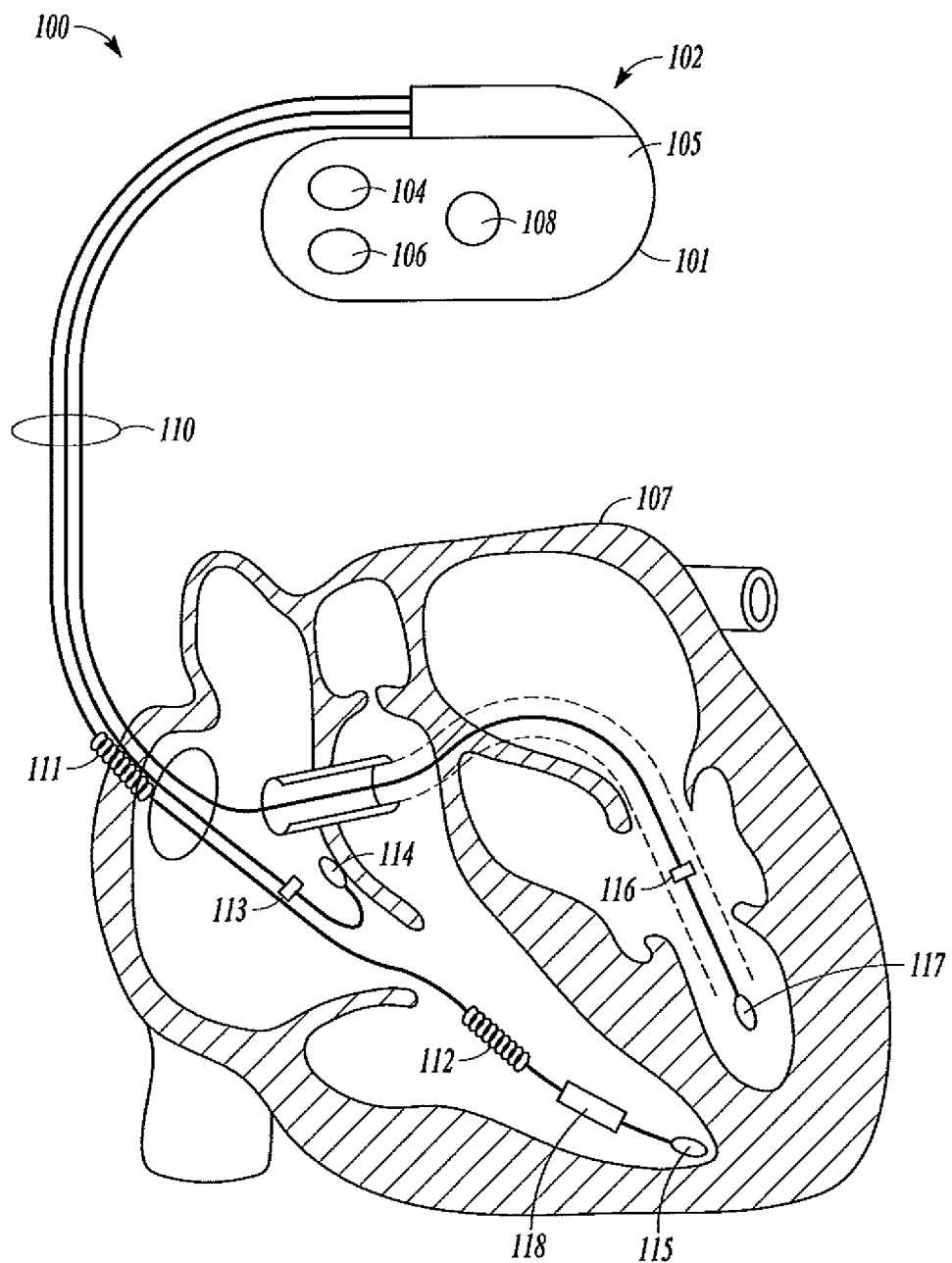
FIG. 1 illustrates generally an example of a portion of a system that can include an implantable or ambulatory medical device, and one or more implantable leads or other electrodes, such as can be configured to be located at least partially in association with cardiac tissue.

FIG. 1 illustrates generally an example of a system 100 that can include an implantable or other ambulatory medical device, such as a cardiac rhythm management (CRM) device 102. In an example, the CRM device 102 can include an implantable electronics unit 105. In an example, the electronics unit 105 can be electrically and physically coupled to an implantable lead system 110.

Portions of the implantable lead system 110 can be inserted into a patient's thorax, including into a patient's heart 107. The implantable lead system 110 can include one or more electrodes that can be configured to sense electrical cardiac activity of the heart, to deliver electrical stimulation to the heart, or to sense the patient's thoracic impedance. In an example, the implantable lead system 110 can include one or more sensors configured to sense one or more other physiological parameters such as cardiac chamber pressure or temperature. Conductive portions of the housing 101 (or attached header) of the electronics unit 105 of the CRM device 102 can optionally serve as an electrode, such as a "can" electrode.

A communications circuit can be included within the housing 101 (or attached header), such as for facilitating communication between the electronics unit 105 and an external communication device, such as a portable or bed-side communication station, a patient-carried or patient-worn communication station, or an external programmer, for example. The communications circuit can also facilitate unidirectional or bidirectional communication with one or more implanted, ambulatory, external, cutaneous, or subcutaneous physiologic or non-physiologic sensors, patient-input devices, or information systems.

The CRM device 102 can include a motion detector 104 that can be used to sense patient physical activity or one or more respiratory or cardiac related conditions. In an example, the motion detector 104 can be configured to sense an activity level or chest wall movements associated with respiratory effort. In an example, the motion detector 104 can include a single-axis or multiple-axis (e.g., three-axis) accelerometer that can be located in or on the housing 101. An accelerometer can be used to provide useful information, including information about patient posture, respiratory information including, for example, about rales or coughing, cardiac information including, for example, S1-S4 heart sounds, murmurs, or other acoustic information.

A processor circuit 108 can be included, such as within the housing 101. In an example, the processor circuit 108 can include a plurality of data inputs configured to obtain physiological data from one or more physiological sensors. For example, the processor circuit 108 can be configured to receive information from the implantable lead system 110, such as via an impedance measurement circuit coupled to a first data input. In an example, first and second data inputs can be configured to receive information from first and second physiological sensors, respectively. In an example, a data input can be configured to receive thoracic impedance data measured using an electrode configuration defining a thoracic impedance vector. Third or fourth data inputs can be configured to receive information from the first and second physiological sensors.

The processor circuit 108 can form a function using one or more received physiological parameters, such as impedance values. This function can be used as a basis from which a plurality of data clusters can be determined. Using the function, the processor circuit 108 can determine at least one quantitative attribute associated with one or more of the data clusters. In an example, the processor circuit 108 can be configured to determine a cardiac decompensation indicator or posture status, such as using one or more of the quantitative attributes. The processor circuit 108 can be configured to trend or otherwise monitor a quantitative attribute of one or more data clusters, such as using a storage circuit.

In an example, the processor circuit 108 can be configured to receive impedance-related information, such as using the implantable lead system 110 to receive voltage levels, Systems and methods describing the acquisition of impedance-related information are further described in Belalcazar, U.S. Pat. No. 7,640,056, entitled "MONITORING FLUID IN A SUBJECT USING AN ELECTRODE CONFIGURATION PROVIDING NEGATIVE SENSITIVITY REGIONS," which is hereby incorporated herein by reference.

In an example, a processor-readable medium can be included, such as within the housing 101. The processor-readable medium can include instructions that, when performed by a processor, configure the CRM device 102 to receive data, process data, interpret data, or provide data, such as using the processor circuit 108. For example, the processor-readable medium can include instructions that, when performed by a processor, configure the CRM device 102 to form a function using impedance information received via a plurality of data inputs to the processor circuit 108.

The storage circuit can be included, such as within the housing 101, for storing a plurality of values, including data trend information. In an example, quantitative attributes of data clusters, such as including range along a y-axis, spread along an x-axis, area, or volume, among others, can be stored in the storage circuit. In an example, the storage circuit can include a histogram-based storage mechanism to facilitate storage of quantitative attributes over an extended period. In an example, the storage circuit can be external to the CRM device 102, or can be communicatively coupled to the CRM device 102 via the communications circuit.

The implantable lead system 110 and the electronics unit 105 of the CRM device 102 can incorporate one or more thoracic impedance or like signal sensors that can be used, for example, to acquire information about a patient's respiratory waveform or other respiration-related information. Illustrative examples of methods of monitoring lung tidal volume by measuring trans-thoracic impedance are described in Hartley et al., U.S. Pat. No. 6,076,015 entitled "RATE ADAPTIVE CARDIAC RHYTHM MANAGEMENT DEVICE USING TRANSTHORACIC IMPEDANCE," which is hereby incorporated herein by reference. Illustrative examples of systems that can detect respiration signals and measure breathing volume are described in Hatlestad et al., U.S. Pat. No. 7,603,170 entitled "CALIBRATION OF IMPEDANCE MONITORING OF RESPIRATORY VOLUMES USING THORACIC D.C. IMPEDANCE," which is hereby incorporated herein by reference.

In an example, the thoracic impedance signal sensor can include, for example, one or more intracardiac electrodes 111-118, such as can be positioned in one or more chambers of the heart 107. The intracardiac electrodes 111-118 can be coupled to an impedance drive/sense circuit 106, such as can be positioned within the housing of the pulse generator 105.

In an example, the impedance drive/sense circuit 106 can be configured to generate a current that flows through the tissue, such as between an impedance drive electrode 131 and a Can electrode on the housing 101 of the electronics unit 105. The voltage at an impedance sense electrode 114 relative to the Can electrode can change as the patient's thoracic impedance changes. The voltage signal developed between the impedance sense electrode 114 and the Can electrode can be detected by the impedance sense circuit 106. Other locations or combinations of impedance sense or drive electrodes are also possible. Some examples are listed in Table 1, and discussed below.

The implantable lead system 110 can include one or more cardiac pace/sense electrodes 113-117, such as can be positioned in, on, or about one or more heart chambers such as for sensing one or more electrical signals from the patient's heart 107. The intracardiac sensing and pacing electrodes 113-117, such as those shown in FIG. 1, can be used to sense or pace one or more chambers of the heart, such as the left ventricle (LV), the right ventricle (RV), the left atrium (LA), or the right atrium (RA). The implantable lead system 110 can include one or more defibrillation electrodes 111, 112 such as for delivering defibrillation or cardioversion shocks to the heart or for sensing one or more intrinsic electrical signals from the heart 107.

Figure 2A:
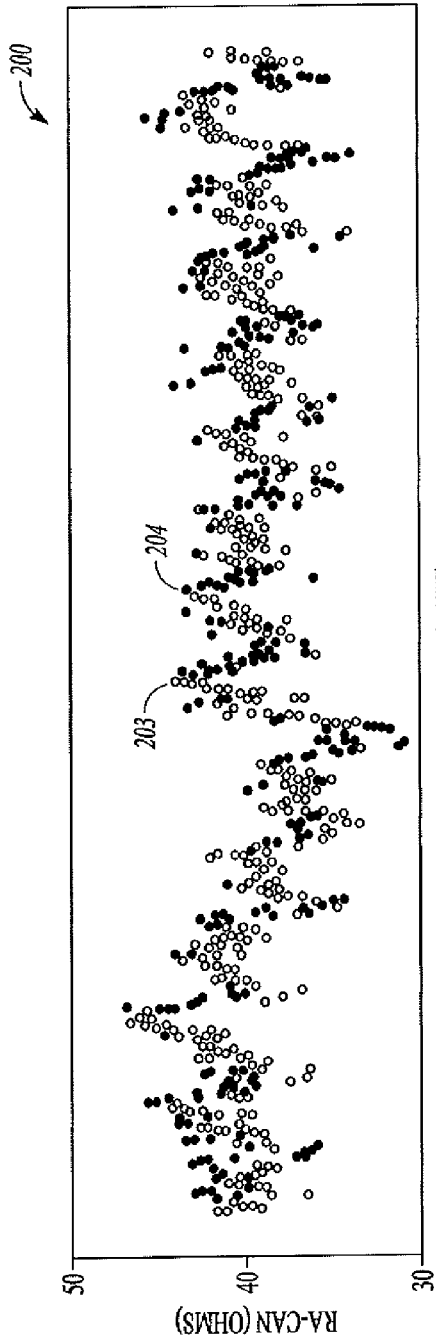
FIG. 2A illustrates generally an example of a graphical representation of thoracic impedance data that can be monitored or recorded over a period of several days.
Figure 2B:
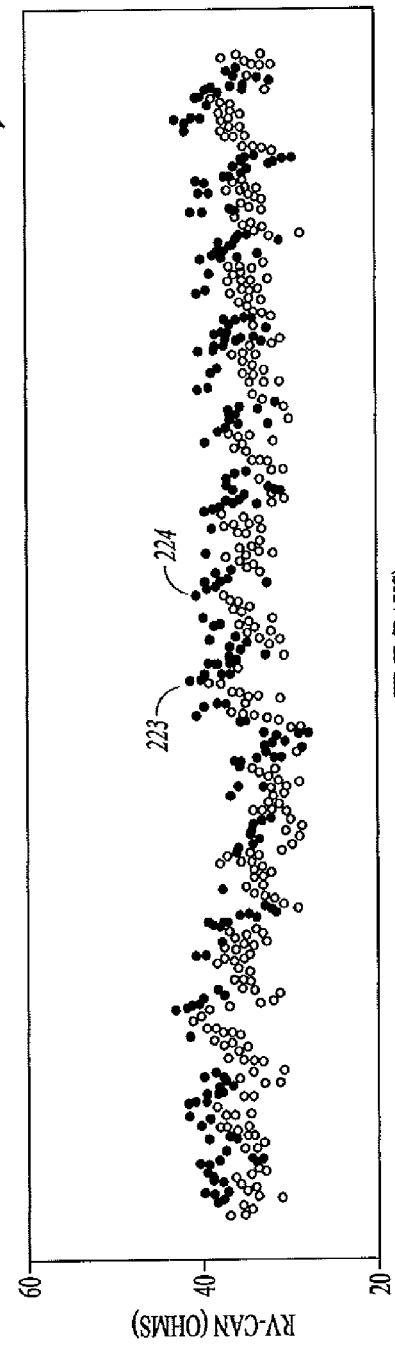
FIG. 2B illustrates generally an example of a graphical representation of thoracic impedance data that can be monitored or recorded over a period of several days.

FIGS. 2A and 2B illustrate generally examples of impedance data such as can be acquired using the implantable lead system 110. In the example of FIG. 2A, the chart 200 illustrates an example of thoracic impedance data such as can be measured using a right atrial (RA) electrode, such as the right atrial impedance sense electrode 114, and a Can electrode. In an example, the RA-Can electrode configuration can indicate a first impedance vector. In the example of FIG. 2B, the chart 220 illustrates an example of thoracic impedance data such as can be measured using a right ventricular (RV) electrode, such as the right ventricular sense electrode 115, and a Can electrode. The RV-Can electrode configuration can indicate a second impedance vector.

Thoracic impedance data can be obtained from a patient at a particular instant in time, or thoracic impedance can be recorded and monitored over a period of time, such as over the course of a day, several days, or longer. In the example of FIGS. 2A and 2B, the data shown in the chart 200 and the chart 220 can represent thoracic impedance data such as can be obtained from a patient over the course of about fourteen days. In an example, thoracic impedance data can be obtained at a sample rate of approximately seventy-two samples per day or one sample every twenty minutes for each monitored impedance vector. Each peak to peak period of the measured impedance data can represent approximately one twenty-four hour period, depending on the activity and physiological parameters of the patient. For example, the period of time defined by the peak 203 and the peak 204 can represent one twenty-four hour period. The data represented in the chart 200 can be obtained over the same fourteen day period as the data represented in the lower chart 240 such that the peak values of the RA-Can impedance measurements correspond in time with the peak values of the RV-Can impedance measurements (e.g., peak 203 occurs at approximately the same time as peak 223, such as within the same sample interval, and peak 204 occurs at approximately the same time as peak 224).

In an example, the data points represented by darkened circles in FIGS. 2A and 2B can represent impedance measurements such as can be obtained while a patient is in a recumbent or lying down posture. The data points represented by unfilled circles in FIGS. 2A and 2B can represent impedance measurements such as can be obtained while a patient is in an upright posture. Although posture can generally be inferred based on time of day, a more accurate posture detection mechanism is available using the impedance information presented in FIGS. 2A and 2B, as explained below. Useful trend information, such as to provide an indication of heart failure decompensation, can also be derived using the impedance information of FIGS. 2A and 2B.

Figure 3:
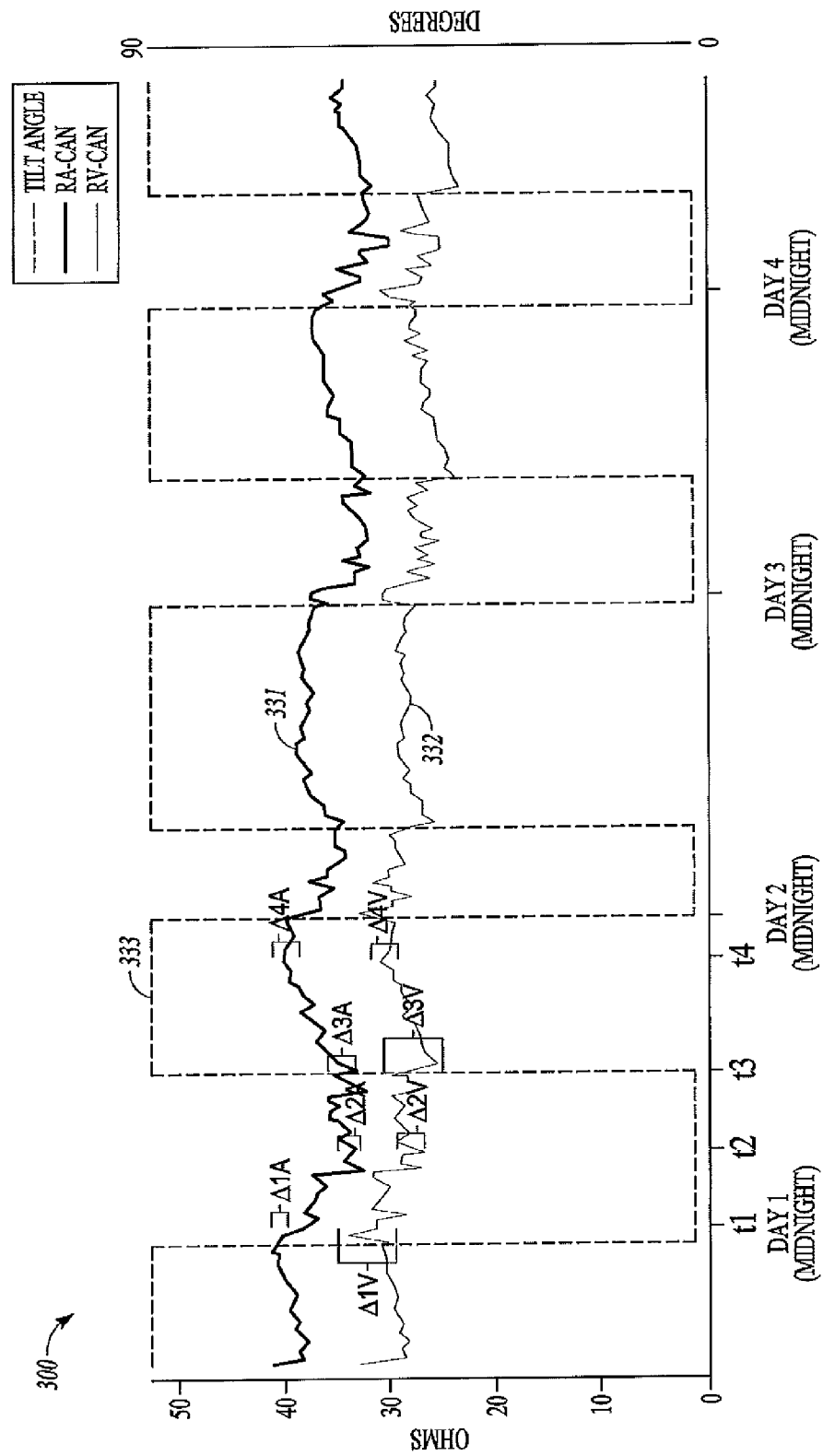
FIG. 3 illustrates generally a graphical representation of thoracic impedance data and posture data that can be obtained over a period of several days.

FIG. 3 illustrates generally an example of a chart 300 illustrating, on common axes, an example of the recorded impedance from the RA-Can and RV-Can impedance vectors such as over a period including approximately four days. The chart 300 includes tilt angle data from a posture sensor, such as the motion detector 104. In the example of FIG. 3, 0 degrees tilt angle can represent a recumbent, supine, or lying down patient position or posture, and 90 degrees tilt angle can represent an upright or standing patient position or posture.

FIG. 3 illustrates generally an example of the thoracic impedance fluctuations that can be expected such as due to patient movement, neurohormonal modulation, or other factors affecting a patient. Generally, the changes in thoracic impedance over time are similarly reflected in more than one measured thoracic impedance vector. In the example of FIG. 3, it can be observed that the change in magnitude of the RA-Can impedance vector 331 from one sample to the next changes by approximately the same magnitude as the RV-Can impedance vector 332 for samples corresponding in time. For example, the change in impedance of the RA-Can impedance vector 331 from the sample preceding $t_2$ to the sample following $t_2$ is $\Delta_{2A}$, or approximately 2 ohms. The change in impedance of the RV-Can impedance vector 332 from the sample preceding $t_2$ to the sample following $t_2$ is $\Delta_{2V}$, which is approximately 2 ohms. Therefore, $\Delta_{2A}$ is approximately equal to $\Delta_{2V}$, and the magnitude of both impedance vectors is modulated by approximately the same amount. Similarly, the change in impedance from the sample preceding $t_4$ to the sample following $t_4$ is $\Delta_{4A}$ for the RA-Can impedance vector 331, and $\Delta_{4V}$ for the RV-Can impedance vector 332, where $\Delta_{4A}$ is approximately equal to $\Delta_{4V}$. In other words, although the RA-Can and RV-Can impedance vectors are expected to change throughout a given time period, such as in response to normal circadian variations, the magnitude of the two vectors can be expected to change by approximately the same amount. That is, generally, $(|RA\text{-}Can_t - RA\text{-}Can_{t-1}|) \approx (|RV\text{-}Can_t - RV\text{-}Can_{t-1}|)$.

At time $t_1$ and $t_3$, however, the change in magnitude of the impedance of the RV-Can impedance vector 332 can be greater than the change in magnitude of the impedance of the RA-Can impedance vector 331. In the example of FIG. 3, time $t_1$ occurs just before midnight, and the posture information or tilt angle indicates that the patient has undergone a change in posture from upright to recumbent, such as when a patient goes to sleep for the night. Immediately following this postural shift, a change in magnitude of the impedance vectors can be observed. It is believed that the change in magnitude of the impedance vectors at the time of a postural change can be attributed to, among other factors, a sudden shift in a patient's thoracic fluid.

In the example of FIG. 3, the change in magnitude of the RA-Can impedance vector 331 is $\Delta_{1A}$, or approximately 1 ohm, and the change in magnitude of the RV-Can impedance vector 332 is $\Delta_{1V}$, or approximately 4 ohms. Thus, a larger change in magnitude of the RV-Can impedance vector 332 as compared to the RA-Can impedance vector 331 can be observed at this patient postural shift. Similarly, at $t_3$, the patient undergoes a second postural shift from a recumbent position to an upright position, such as when a patient wakes for the day. The change in impedance from the sample preceding $t_3$ to the sample following $t_3$ is $\Delta_{3A}$ for the RA-Can impedance vector 331 and $\Delta_{3V}$ for the RV-Can impedance vector 332. Again, a change in magnitude of the RV-Can impedance vector 332, $\Delta_{3V}$, is greater than the change in magnitude of the RA-Can impedance vector 331, $\Delta_{3A}$.

Figure 4A:
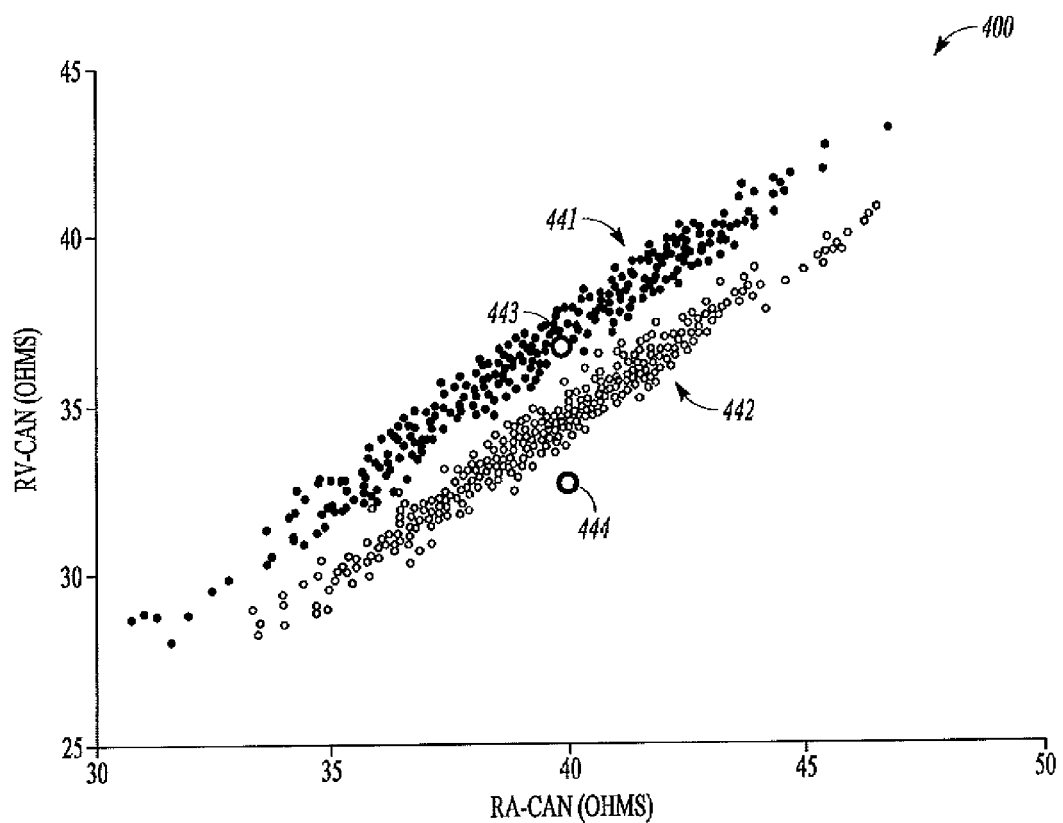
FIG. 4A illustrates generally a graphical representation of a function for which first thoracic impedance data from a first impedance vector can be plotted against second thoracic impedance data from a second impedance vector.

FIG. 4A illustrates generally an example of a chart 400 using a Cartesian coordinate system wherein information from a first physiological sensor can be plotted against information from a second physiological sensor. In the example of FIG. 4A, impedance data from the RA-Can impedance vector 331 can be plotted, such as along an x-axis, against impedance data from the RV-Can impedance vector 332, such as along a y-axis. Impedance magnitude samples obtained at corresponding times, or within corresponding sample windows, form the coordinates of the plotted impedance data.

In the example of FIG. 4A, a first time interval $0 < t < 1$ can include an impedance magnitude measurement for each of the RA-Can impedance vector 331 and the RV-Can impedance vector 332. The magnitude of the first impedance data obtained during the first time interval can be plotted against the second impedance data obtained during the same first time interval. Additional impedance magnitude data can be added for subsequent time intervals, such as every half hour.

FIG. 4A is an example illustrating approximately four days of impedance information from a single patient, such as using the impedance information shown in FIG. 3. In an example, the impedance data shown in FIG. 4A can be sampled at a rate of one sample every twenty minutes, for a total of 288 data points over a four day period. In FIG. 4A, the impedance data from the RA-Can vector and the RV-Can vector can be plotted on the Cartesian plane, forming at least two data clusters. The data clustering can occur because of the difference in the change of magnitude in the first vector (e.g. $\Delta_{1A}$) as compared to the second vector (e.g. $\Delta_{1V}$) at patient posture changes. The data clusters can be subsets of the original data. The division or assignment of the original data to a data cluster can be accomplished using any one or more of several clustering techniques, such as using a computer processor to execute instructions to perform a clustering technique. Several clustering techniques can be used, including hierarchical clustering (e.g., involving dividing a large set of data into successively smaller clusters), partitional clustering (e.g., involving a determination of a belonging-factor for each point to each cluster), or density-based clustering (e.g., involving identifying areas of high density). Each cluster can represent a portion of the function formed using information from two or more physiological sensors.

Referring now to FIGS. 3 and 4A, the impedance data of the RA-Can impedance vector 331 and the RV-Can impedance vector 332 for $t < t_1$ can be represented in the lower cluster 542 of FIG. 4A. At time $t=t_1$, the change in magnitude of the RV-Can impedance vector 332, $\Delta_{1V}$, is greater than the change in magnitude of the RA-Can impedance vector 331, $\Delta_{1A}$. This difference in the change in magnitude can cause a jump from the lower cluster 442, corresponding to an upright patient position, to the upper cluster 441, corresponding to a recumbent patient position. Impedance data acquired during time $t_1 < t < t_2$, such as corresponding to a recumbent patient position, can fall into the upper cluster 441. At time $t=t_3$, a patient posture shift, such as returning the patient to an upright position, can cause another jump. The jump can be from the upper cluster 441 to the lower cluster 442. Impedance data acquired for $t > t_3$ can fall into the lower cluster 442, corresponding to an upright patient position.

In an example, the chart 400 can include first physiological data obtained using a first physiological sensor, and second physiological data obtained using a second physiological sensor. In an example, the first and second physiological data can be acquired over time, and the time variable can be removed from the chart 400 by plotting the first physiological data against the second physiological data.

The physiological sensors can include sensors configured to measure electrical characteristics such as voltage or impedance, or sensors configured to measure mechanical or acoustic information, among others. In an example, three or more physiological sensors, such as three different implantable electrodes, can be used to monitor three different impedance vectors in a patient. In an example, two physiological sensors can be configured to monitor two different impedance vectors, and a third physiological sensor can be configured to monitor S3 heart sounds. The data from the two or more physiological sensors can be used to form a function, such as a function of the first physiological data against the second or third physiological data. The function can be used to form data clusters, such as by determining discrete portions of the function, such as by plotting the data in a time-independent manner.

In an example, the chart 400 can include a third impedance vector, such as using a left-ventricular electrode and a Can electrode. This third impedance vector can be plotted against the RA-Can impedance vector 331 and RV-Can impedance vector 332 to form three dimensional data clusters. Additional sensor data can be plotted against the three dimensional data clusters such as to form a multi-dimensional function.

Figure 4B:
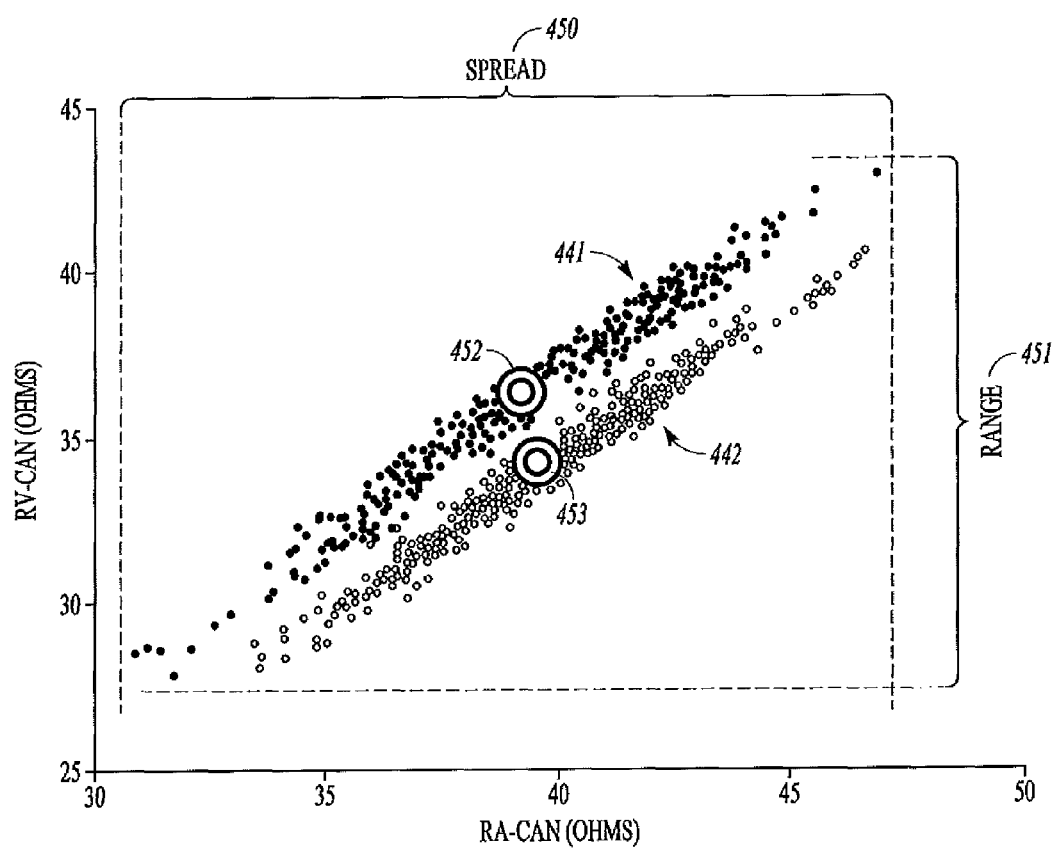
FIG. 4B illustrates generally a graphical representation of a function that can include one or several quantitative attributes of the function, such as centroid location, spread, or range.

FIG. 4B illustrates generally several of the characteristics or quantitative attributes of the chart 400. Some examples of the characteristics can include spread along an x-axis, range along a y-axis, and data cluster centroid location. Some characteristics of multi-dimensional functions, such as can be formed using data from two or more sensors, can include spread, range, area, volume, and hyper-volume (in the case of four-dimensional, or higher dimensional, space), among other attributes.

In an example, the spread 450, such as along an x-axis, of one or both of the data clusters 441, 442 can be measured. The spread 450 of the data clusters can represent the domain of all the impedance magnitude values attributed to a particular vector, such as the RA-Can impedance vector 331. In the example of FIG. 4B, the spread of the lower cluster 442 can be 33 ohms to 46 ohms. In an example, the difference between the maximum impedance and the minimum impedance can represent the spread 450. In the example of FIG. 4B, the spread 450 can be 13 ohms for the lower cluster 442, and the spread 450 can be 16 ohms for the upper cluster 441. In the example of FIG. 4B, the spread 450 of the upper cluster 441 can be equal to the spread 450 of the entire function represented on the chart 400. In an example, the spread 450 can represent a standard deviation or variance of the impedance values of the data points within a cluster.

FIG. 4B illustrates generally an example of the range 451 of the function represented on the chart 400. The range 451 can represent the range of the entire function represented on the chart 400, or the range 451 can represent a portion of the function, such as including the range of one or more data clusters. In the example of FIG. 4B, the range 451 of the upper cluster 441 can be approximately 15 ohms. In an example, the range of the lower cluster 442 can be approximately 13 ohms. In an example, the range 451 can represent a standard deviation or variance of the impedance values of the data points within a cluster.

In an example, the range and spread of the function can be combined, such as using the Pythagorean Theorem, to obtain a range of the function over multi-dimensional space. For example, the range and spread of the function can be combined using the equation $\sqrt{(spread(x))^2 + (range(y))^2}$, where spread(x) is the overall spread of the data along the x-axis, and range(y) is the overall range of the data along the y-axis.

Quantitative attributes of the data, such as the centroids of the data clusters, the distance between centroids of the data clusters, or the area of one or more data clusters, among other attributes, can also be measured using the chart 400. FIG. 4B illustrates generally the centroid 452 of the upper cluster 441 and the centroid 453 of the lower cluster 442. The centroid of the upper cluster 441 can be located, for example, at coordinates:

$$\left( RA-Can = \frac{\sum_{i=1}^{n}(RA-Can)_i}{n}, RV-Can = \frac{\sum_{i=1}^{n}(RV-Can)_i}{n} \right),$$

where n is the number of RA-Can impedance measurements attributed to the upper cluster 441, and $(RA-Can)_i$ is the magnitude of the impedance measurement attributed to sample i.

The distance between the centroids of the upper cluster 441 and lower cluster 442 can be determined such as using the Pythagorean Theorem. In general, the centroid analysis can be extended to any number of clusters, including clusters in three dimensional space, such as can be plotted using data from an additional sensor or impedance vector. The coordinate of the centroid in the third dimension can be:

$$Sensor = \frac{\sum_{i=1}^{n}(sensor)_i}{n},$$

where n is the number of measurements from the third sensor attributed to the upper cluster 441, and $(sensor)_i$ is the magnitude of the measurement from the third sensor attributed to sample i.

In an example, analyzing one or more vectors associated with a centroid can provide quantitative attribute information. For example, a vector associated with the origin and the centroid 452 can be compared with a vector associated with the origin and the centroid 453. In an example, a dot product of two or more vectors can be performed to obtain the quantitative attribute including the angle between the vectors.

Figure 4C:
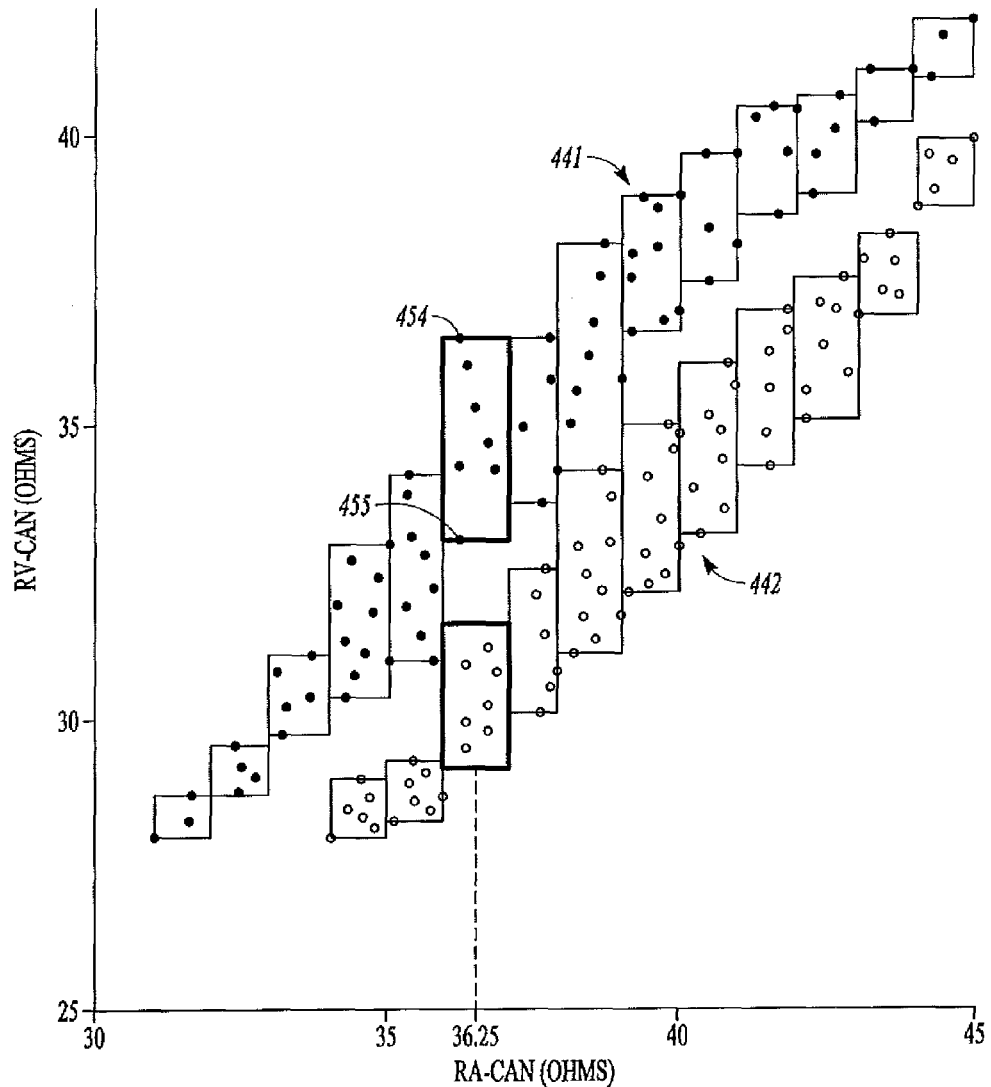
FIG. 4C illustrates generally a graphical representation of a numerical integration method that can be used to calculate an area of one or more data clusters.

There are several methods of calculating the area of a data cluster, such as by integrating a function or set of functions representative of the data, or by numerical integration techniques, among others. FIG. 4C illustrates generally a method of calculating the area of a data cluster by numerical integration. The spread or range of the data can be divided into n discrete intervals, and a local minimum and maximum can be found for each interval to define the extents of a rectangle. The areas of the rectangles can be determined and summed to provide an approximation of total cluster area. In the example of FIG. 4C, the data clusters can each be divided into fourteen intervals of 1 ohm each. The data points in the sixth interval of the upper cluster 441 include a local minimum 455 at (RA-Can=36.3, RV-Can=33), and a local maximum 454 at (RA-Can=36.25, RV-Can=36.5) to define a rectangle of area 3.5 (units omitted). The area of the rectangle in the sixth interval of the lower cluster is 2.25 (units omitted). The total area of the upper cluster, calculated using this method, is approximately 29.25, and the total area of the lower cluster is approximately 22.5.

Figure 4D:
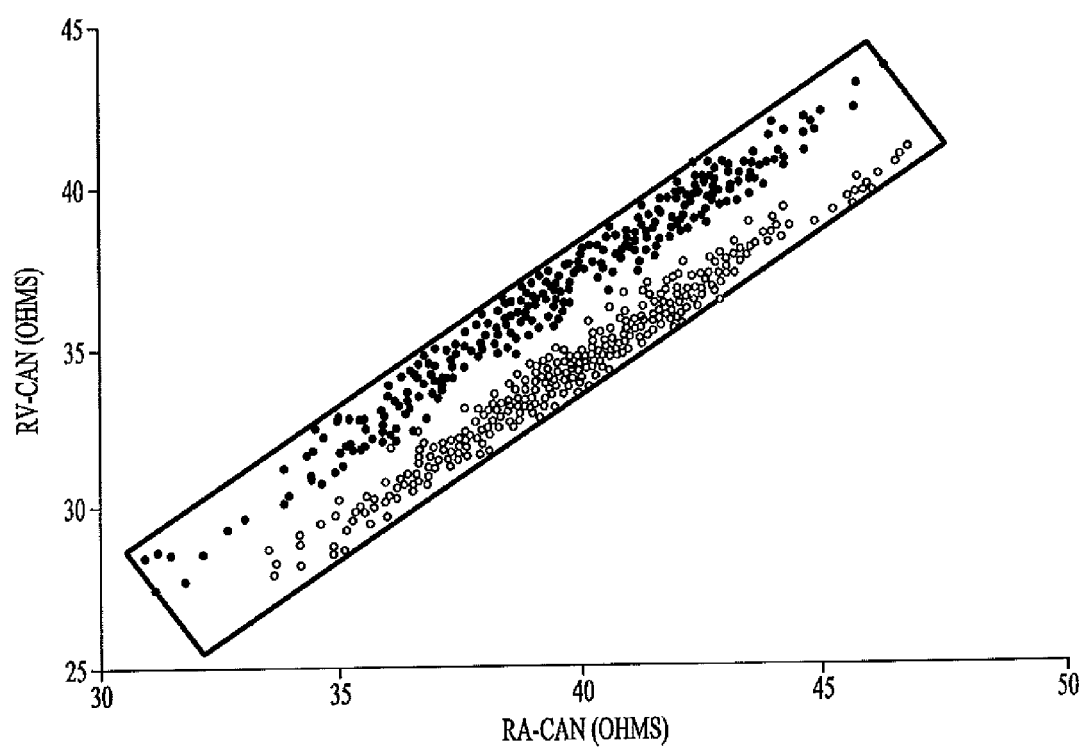
FIG. 4D illustrates generally a graphical representation of a method that can be used to calculate an area of one or more data clusters, such as by finding the extents of the data and drawing a rectangle.

The area of the set of data clusters can also be calculated, such as using the method depicted in FIG. 4D. A rectangle can be drawn completely encapsulating the data clusters. In the example of FIG. 4D, the total area of the rectangle encapsulating the data clusters is approximately 74. Several other techniques for calculating or approximating the total area of the data clusters can be used, such as the numerical integration method described above in the discussion of FIG. 4C.

In an example, the area of a pair of data clusters can be calculated using the equation:

$$\text{area}=d\sqrt{(\text{spread}(x))^2+(\text{range}(y))^2},$$

where d is the distance between the centroids of the two clusters, spread(x) is the overall spread of the data along the x-axis, and range(y) is the overall range of the data along the y-axis. In this example, it is assumed that the data clusters can be represented as a quadrilateral with two opposite sides of length $\sqrt{(\text{spread}(x))^2+(\text{range}(y))^2}$, and a distance between these two opposite sides equal to the distance between the centroids.

Other data cluster analysis techniques can be used. For example, a least-squares technique can be used to regress a best-fit line to one or more data clusters. The slope of a best-fit line can be used as a quantitative attribute, or the area under a portion of a best-fit line can be used. Other techniques for regressing higher order best-fit curves to one or more data clusters can also be used.

Data cluster density, such as over a particular range or spread, can be monitored over time. Changing densities or the locations of densities can be used as quantitative attributes to provide patient diagnostic information. In an example, a function indicative of density can be formed and analyzed to determine a quantitative attribute.

FIGS. 4A through 4D illustrate generally non-limiting examples of several of the quantitative attributes of the data clusters 441 and 442. These examples should not be seen as limiting the scope of the present subject matter. There are numerous ways of calculating the quantitative attributes associated with data clusters.

Various methods for acquiring and representing physiological data have been described with respect to a first patient physiology, such as a physiology with no present indication of cardiac decompensation. In a second patient physiology, such as a diseased physiology, the physiological data can differ substantially from the first physiology. For example, the magnitude of the modulation of a particular thoracic impedance vector can differ substantially between the first patient physiology and the second.

Figure 5:
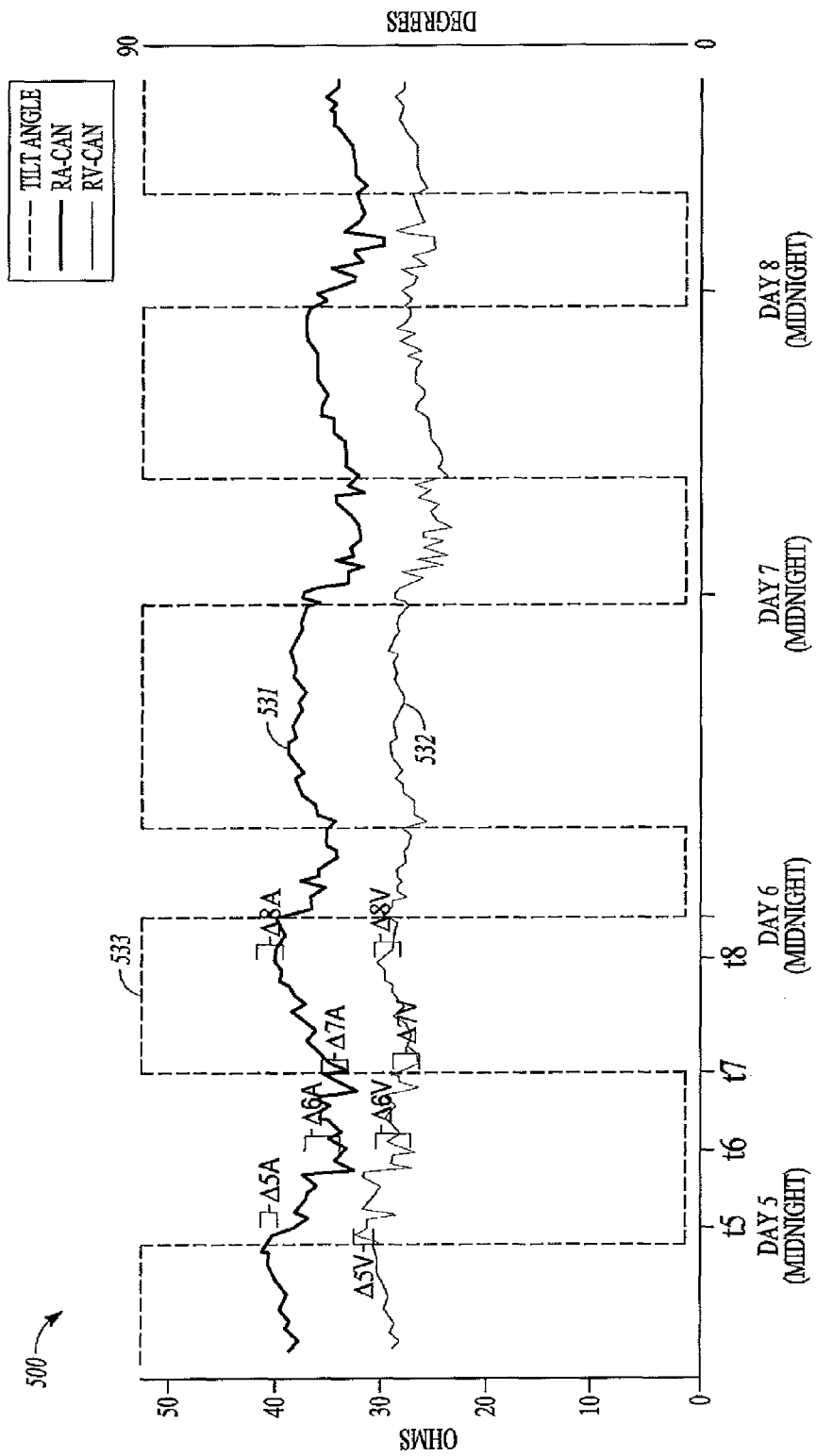
FIG. 5 illustrates generally a second graphical representation of thoracic impedance data and posture data over a period of several days.

FIG. 5 illustrates generally an example of a chart 500 illustrating an example of impedance vectors and patient posture data from a patient at increased risk of heart failure decompensation. The chart 500 illustrates a period including approximately four days during which posture information is recorded, and impedance data is recorded for a patient's RA-Can impedance vector 531 and RV-Can impedance vector 532. In the example of FIG. 5, the RV-Can impedance vector 532 does not exhibit significant changes in magnitude near or at patient posture changes.

As in FIG. 3, FIG. 5 illustrates the thoracic impedance fluctuations that can be expected due to patient movement, neurohormonal modulation, or other factors affecting the patient. However, the impedance vectors depicted in FIG. 5 can indicate a diseased patient state, such as a patient experiencing pulmonary edema. In particular, the difference in the change in magnitude of the RA-Can impedance vector 531 as compared to the RV-Can impedance vector 532 is decreased or minimized at patient posture changes.

For example, at $t_5$ and $t_7$, the change in magnitude of the impedance of the RV-Can impedance vector 532 is no longer as starkly contrasted with the change in magnitude of the impedance of the RA-Can impedance vector 531. In the example of FIG. 5, time $t_5$ occurs just prior to midnight, and the posture information indicates that the patient has undergone a change from an upright to recumbent posture, such as when a patient goes to sleep for the night. Immediately following this postural shift, the large change in magnitude of the RV-Can impedance vector 332, as observed in FIG. 3 at $\Delta_{1V}$, is reduced or is no longer present.

In an example, the change in magnitude of a patient's RA-Can or RV-can impedance vectors at the time of a postural change can be attributed to, among other factors, a local shift in a patient's thoracic fluid. Thoracic fluid in an upright patient can tend to accumulate in lower regions of the body due to the normal response of fluid due to gravity. When the patient enters a recumbent or lying down posture, fluid can disperse in the thorax, including in the cardiac region. Fluid accumulation in the region of implanted electrodes can contribute to a change in impedance detected using those electrodes, such as an increase in thoracic admittance during the night due to fluid accumulation in the lungs. A patient experiencing pulmonary edema, such as can be caused by venous congestion associated with congestive heart failure, can exhibit an abnormal accumulation of thoracic fluid. As fluid accumulates, however, the magnitude of normal fluid shift between upright and recumbent postures decreases. That is, because the fluid level can be elevated in the diseased state, the fluid may not shift as much when a patient changes posture. If a pulmonary region is saturated with fluid, changes in the magnitude of measured thoracic impedance vectors due to patient posture changes can be decreased. A fluid shift can be reflected more readily in some vectors than in others.

In the example of FIG. 5, the change in magnitude of the RA-Can impedance vector 531 at $t_5$ is $\Delta_{5A}$, or approximately 1 ohm, and the change in magnitude of the RV-Can impedance vector 532 is $\Delta_{5V}$, or approximately 1 ohm. The change in magnitude of the RV-Can impedance vector 532 at $t_5$ is notably less than the change in magnitude of the RV-Can impedance vector 332 at $t_1$. This substantive difference at similar posture shifts can indicate an increased thoracic fluid level. Similarly, at $t_7$, the patient undergoes a second postural shift, from a recumbent to an upright posture. The change in magnitude of the impedance from the sample preceding $t_7$ to the sample following $t_7$ is $\Delta_{7A}$ for the RA-Can impedance vector 531 and $\Delta_{7V}$ for the RV-Can impedance vector 532. Importantly, the change in magnitude of the RV-Can impedance vector 532, $\Delta_{7V}$, is less than the change in magnitude of the RV-Can impedance vector 332, $\Delta_{3V}$.

Figure 6:
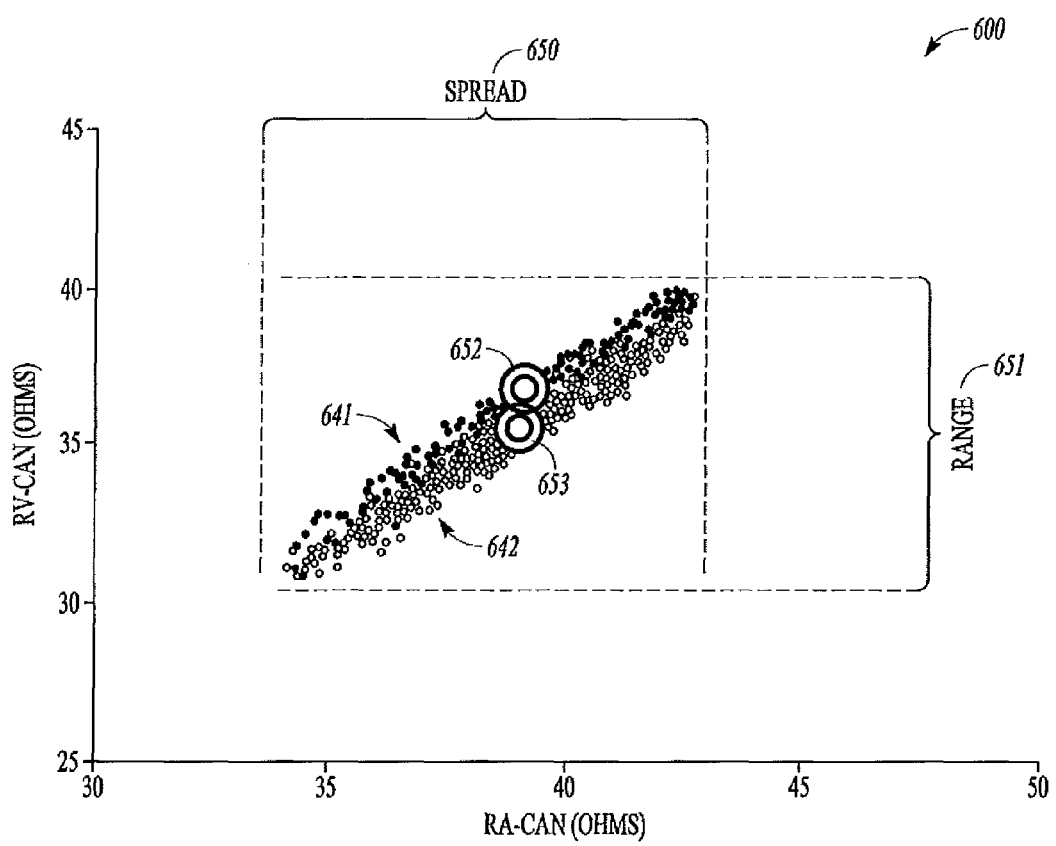
FIG. 6 illustrates generally a graphical representation of a second function including several quantitative attributes of the function.

FIG. 6 illustrates generally an example of a second chart 600 wherein impedance data from the RA-Can impedance vector 531 can be plotted against corresponding impedance data from the RV-Can impedance vector 532. As in FIG. 4A, when the impedance data for the two vectors is plotted against each other to remove time as a chart axis variable, the data can form clusters. However, in the example of FIG. 6, the data can indicate an elevated fluid level, such as pulmonary edema due to worsening heart failure. Comparing FIGS. 6 and 4A, the clusters in the second chart 600 are not as clearly distinguishable as they are on the chart 400. Because of the reduction in magnitude of the difference in the change in a first vector (e.g. $\Delta_{5V}$) as compared to a second vector (e.g. $\Delta_{5A}$) at patient posture shifts, the clusters approach each other in the RA-Can/RV-Can Cartesian plane. In an example, the cluster boundaries can become indistinguishable. The upper cluster 641, representative of a first posture, can be indistinguishable from the lower cluster 642, representative of a different posture.

In the example of FIG. 6, the impedance modulation of the vectors due to normal circadian variations over the four-day period can be reduced in magnitude compared to the modulation observed in the vectors over a different period, such as including a healthy, non-edemic state. For example, the magnitude of the impedance changes on day six at $\Delta_{8A}$ and $\Delta_{8V}$ can be less than the magnitude of the impedance changes at a similar time on day two, such as at $\Delta_{4A}$ and $\Delta_{4V}$ in FIG. 4A. The change in magnitude of the impedance changes can be indicative of different patient physiological states. The reduced impedance modulation of FIG. 6, as compared to FIG. 4A, can be observed in the spread and range of the data clusters in the second chart 600. The spread and range are each reduced from the different physiological state represented in the chart 400. For example, the spread of the upper cluster 441 is 17 ohms, and the spread of the upper cluster 641 is 10 ohms.

The quantitative attributes of data clusters formed using recently acquired data can be compared with attributes of data clusters formed using previously acquired data, such as to detect a change in patient physiology. Such changes can be monitored by monitoring quantitative attributes of data clusters associated with several discrete bundles of physiological data, such as weekly or daily physiological data. Quantitative attributes of data clusters can, in an example, be monitored or trended using the processor circuit 108 over any period of time, such as to identify one or more trends in patient etiology. For example, data cluster analysis over time can be used to indicate a diseased or at-risk patient state. This can include providing a heart failure decompensation indicator. Data cluster attribute information can be stored in any number of formats, such as in a histogram to facilitate storage of a large amount of data.

One or several quantitative attributes of the data clusters can be analyzed and trended, such as area, centroid location, spread, or volume, among others. In an example, the area of one or both data clusters in the second chart 600 can be compared to the area of one or both data clusters in the chart 400. In an example, the upper cluster 641 can be compared to the upper cluster 441. The area of one or both data clusters in the second chart 600 can be compared to a trend of cluster areas including more than one previous cluster area. Where three physiological sensors are used to obtain a three-dimensional function, the volume of a data cluster can be trended. In an example, four or more physiological sensors can be used to obtain a multi-dimensional function. Quantitative attributes of clusters defined by the multi-dimensional function can be trended. In an example, trending one or more quantitative attributes can include monitoring and recording quantitative attributes for a series of data clusters obtained during several time windows, such as consecutive time windows.

The centroid locations of the data clusters 641, 642 can be compared to the centroid locations of previously recorded data. For example, the location of the centroid 652 can be compared to the location of the centroid 452. In an example, the change in location of the centroid of a data cluster associated with a particular patient posture can indicate a physiological trend, such as an increased risk for cardiac decompensation. The location of the centroid 652 can be compared to a series of previous centroid locations associated with an upper data cluster, such as to find a trend in upper data cluster centroid location.

The distance between two or more centroids can be recorded and trended over a period of time, such as to indicate one or more changes in a patient's physiological state. A first distance between the centroids 452 and 453 can be determined, such as using the Pythagorean Theorem. A second distance between the centroids 652 and 653 can be similarly determined. The distance between any number of centroids representative of data clusters reflecting several postures can be calculated and trended. In an example, a decreased distance between a first and second distance can indicate an abnormal patient state, such as present or impending heart failure decompensation associated with pulmonary edema.

Minima and maxima for each data cluster can be trended, or the range or spread of the data clusters can be trended over time. For example, the spread 450 of the upper data cluster 441 can be compared to the spread 650 of the upper data cluster 641, or it can be compared to a trend of the spreads of a series of upper data clusters. The spread 450 of the function represented in the chart 400 can be compared to the spread 450 of the function represented in the second chart 600, or a trend of the spreads of several functions. In an example, the reduced spread in the second chart 600 compared to the chart 400 can be indicative of a patient physiological change.

In an example, a baseline physiological patient state can be established, such as including a baseline data cluster quantitative attribute. The baseline data cluster quantitative attribute can include a baseline distance between data cluster centroids for different data clusters representing upright and recumbent postures. A change from the baseline distance that exceeds some threshold distance can, in an example, send an alert to a patient or clinician to provide an early indication of a potential abnormal state.

Figure 7:
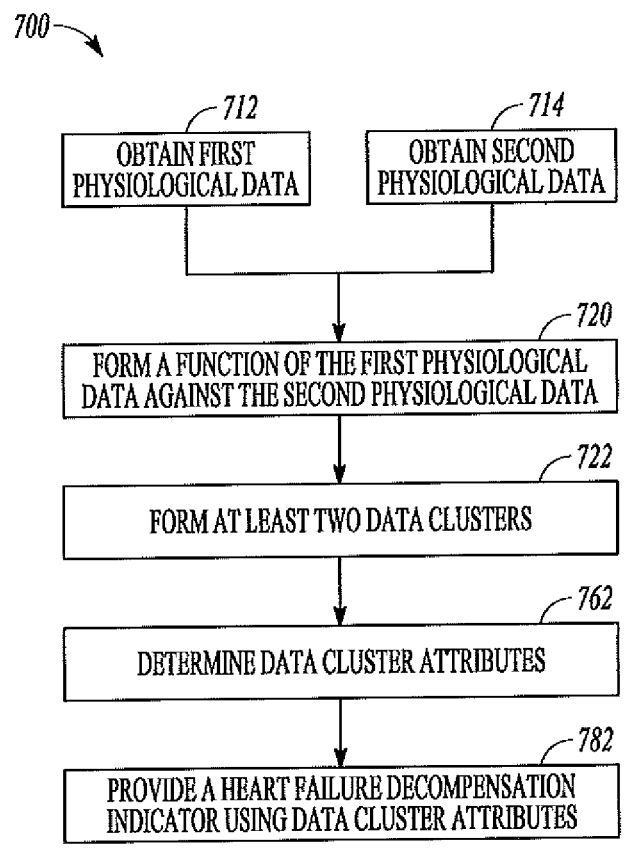
FIG. 7 illustrates generally an example that can include providing a heart failure decompensation indicator using data cluster attributes.

FIG. 7 illustrates generally an example 700 that can include obtaining first physiological data 712, obtaining second physiological data 714, forming a function of the first physiological data against the second physiological data 720, forming at least two data clusters 722, determining data cluster attributes 762, and providing a heart failure decompensation indicator using data cluster attributes 782.

At 712, first physiological data can be obtained. At 714, second physiological data can be obtained. Obtaining physiological data can include one or more of obtaining data indicative of an electrical characteristic of a patient, data indicative of a mechanical characteristic of a patient, or data indicative of a present patient status, Data indicative of an electrical characteristic can include information indicative of impedance, intrinsic tissue signals, capacitance, or admittance, among other types of information. Data indicative of a mechanical characteristic can include information indicative of patient motion, acoustic information including heart sounds, or respiratory information, among other types. Data indicative of a present patient status can include information about a patient posture, or a patient activity level, among other types.

In an example, obtaining first physiological data 712 can include obtaining a thoracic impedance measurement using electrodes located on or in a patient body. Implantable electrodes installed in or near a heart wall can be used, such as the right ventricular sense electrode 115. A second electrode, such as a Can electrode, can be located elsewhere, such as in the chest or abdomen of a patient. A first impedance vector, such as between the right ventricular sense electrode 115 and the Can electrode, can be used to obtain the thoracic impedance measurement. Several other vectors that can be used to obtain physiological data are presented in Table 1, where an "X" indicates a possible vector between the corresponding first and second electrodes. In Table 1, Can refers to the conductive housing of an implantable device, RA refers to one or more electrodes located in or near the right atrium of the heart, RV refers to one or more electrodes located in or near the right ventricle of the heart, LV refers to one or more electrodes located in or near the left ventricle of the heart, SV refers to one or more electrodes located in or near a supraventricular region of the heart, Connector Block refers to a lead connector block (e.g., "header") electrode, such as on the CRM 102, that is independent of the Can electrode, and Intravascular Cathode refers to one or more electrodes located in an intravascular location outside of the heart. In an example, obtaining a thoracic impedance measurement can include averaging or otherwise computing a central tendency of the total measured impedance such that impedance variations due to cardiac stroke or respiration are largely omitted.

TABLE 1

Impedance vectors used to obtain physiological data.

|  |  | First Electrode | | | | | |
|---|---|---|---|---|---|---|---|
|  |  | RA | RV | LV | SV | Connector Block | Intravascular Cathode |
| Second Electrode | Can | X | X | X | X |  | X |
|  | RA |  | X | X | X | X | X |
|  | RV |  |  | X | X | X | X |
|  | LV |  |  |  | X | X | X |
|  | SV |  |  |  |  | X | X |
|  | Connector Block |  |  |  |  |  | X |

In an example, obtaining first physiological data 712 can include obtaining heart sound information using a sensor, such as an accelerometer, configured to detect S3 heart sound information. The first physiological data can include electrical signals from the accelerometer indicative of mechanical vibrations of the heart.

At 720, a function can be formed using the first physiological data and the second physiological data. In an example, the first physiological data can be used as a domain of values, and the second physiological data can be used as a range of values. Each value in the domain can correspond to a value in the range, such as by pairing values obtained at the same time, or obtained during a common time interval or window. In an example, the first and second physiological data can be plotted against each other on common axes. Where the first and second physiological data are obtained in a time-dependent manner, the plot of the first physiological data against the second can remove time as an explicit variable in the function that is formed.

At 722, one or more data clusters can be formed. In an example, the data clusters can be obtained from the function formed at 720. One or more of several clustering techniques can be used, such as described above in the discussion of FIG. 5A. In an example, two impedance vectors can be used to form the function, and at least two data clusters can be discerned from the function. The number of data clusters can be limited, if desired, such as by the clustering technique or the available processor capacity. In an example, only a single cluster can be discerned from the function using the available clustering techniques.

In an example including two data clusters obtained from the function using two impedance vectors, one cluster can correspond to a rising phase, or build-up phase, phase of the measured impedance throughout the waking portion of a patient's day. During a build-up phase, the impedance data can correspond to a first data cluster, and during a decreasing phase, the impedance data can correspond to a different data cluster. Depending on patient posture, the impedance can tend to be higher or lower in average magnitude, and can tend to build up and decrease over time in an approximately periodic or other recurrent manner, such as illustrated in FIGS. 2, 3 and 5.

At 762, one or more data cluster attributes, such as spread, range, mean, centroid location, area, density, or volume, can be determined. Several non-limiting methods for determining data cluster attributes are included in the discussion of FIGS. 5A, 5B, 5C, and 5D.

At 782, a heart failure decompensation indicator can be provided using one or more data cluster attributes. In an example, any one or more of the quantitative attributes such as spread, range, mean, centroid location, distance between two or more centroids, area, density, or volume of a data cluster, alone or in combination, can be used to provide a heart failure decompensation indicator. In an example, a comparison of one or more quantitative attributes associated with a first time window with one or more quantitative attributes associated with a different time window can be used to provide the heart failure decompensation indicator. Below, the discussion of FIG. 8 includes several examples of using a data cluster attribute to determine an abnormal or diseased state, such as determining a heart failure decompensation indicator.

Figure 8:
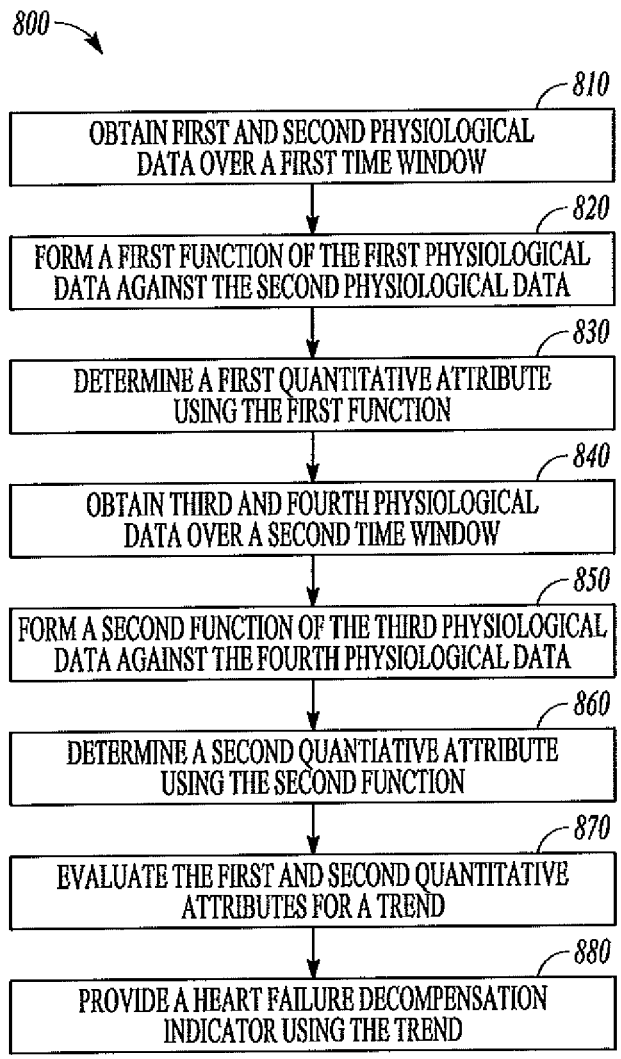
FIG. 8 illustrates generally an example that can include determining first and second attributes using respective first and second functions of different physiological data, obtaining first and second physiological data over a first time window, trending the first and second attributes, and providing a heart failure decompensation indicator using the trend.

FIG. 8 illustrates generally an example 800 that can include obtaining first and second physiological data over a first time window 810, forming a first function of the first physiological data against the second physiological data 820, determining a first quantitative attribute using the first function 830, obtaining third and fourth physiological data over a second time window 840, forming a second function of the third physiological data against the fourth physiological data 850, determining a second quantitative attribute using the second function 860, evaluating the first and second quantitative attributes for a trend 870, and providing a heart failure decompensation indicator using the trend 880.

At 810, first and second physiological data can be obtained over a first time window. Obtaining physiological data can include one or more of obtaining data indicative of an electrical characteristic of a patient, data indicative of a mechanical characteristic of a patient, or data indicative of a present patient status, wherein the physiological data can be obtained during a discrete time interval. A first physiological sensor can be used to obtain the first physiological data, and a second physiological sensor can be used to obtain the second physiological data. The first and second physiological sensors can be electrodes in the implantable lead system 110.

In an example, the first and second physiological data can be obtained at any instant or at multiple instances over a first time window, such as over a first twenty minute window. For example, the first and second physiological data can be obtained by averaging or computing another central tendency of a series of measurements in a twenty minute window, or by saving maximum- or minimum-valued measurements occurring in the twenty minute window. The window duration and the number of data collection instances over that window can be any appropriate duration or number that will permit accurate collection of physiological data. For example, an impedance measurement can be taken using the implantable lead system 110 as the average or other central tendency of impedance over several milliseconds. A measurement to detect heart wall motion can involve a several second window, such as to detect a muscular response to an electrical stimulation.

At 820, a first function of the first physiological data can be formed against the second physiological data. The first function can be formed such as according to the discussion of FIG. 7 at 720. In an example, a portion of the first function can determine at least a first pair of data clusters.

At 830, a first quantitative attribute can be determined using the first function. The first quantitative attribute can include any attribute of the first function, such as including the range, domain, or periodicity of the function, among other attributes. The first quantitative attribute can be derived from one or more data clusters, such as the first pair of data clusters, formed using one or more portions of the function. For example, the function can describe several data clusters, and a first quantitative attribute can include the area of a particular data clusters.

At 840, third and fourth physiological data can be obtained over a second time window. The third and fourth physiological data can be obtained in the same manner as the first and second physiological data, although the third and fourth physiological data can correspond to a different time interval. In an example, the first and third physiological data can be obtained using the same physiological sensor, such as an accelerometer configured to obtain heart sound information. The second and fourth physiological data can be similarly obtained using the same physiological sensor, such as an implantable electrode located in the thorax of a patient. In an example, the second time window can be a different duration than the first time window. Different time window durations or sampling rates can be used to increase or decrease data collection at particular times. For example, an increased sampling rate can be used when a particular event is expected, such as a patient posture change. A reduced sampling rate can be used, for example, when a patient is sleeping or stationary.

At 850, a second function can be formed using the third and fourth physiological data. The second function can be formed in the same manner as the first function, as described above in the discussion of FIG. 8 at 820. In an example, a portion of the second function can determine at least a second pair of data clusters.

At 860, a second quantitative attribute, such as a test quantitative attribute, can be determined using the second function. The second quantitative attribute can include any attribute of the second function, such as including the attributes described in this discussion at 830. In an example, the second quantitative attribute can be derived from the second pair of data clusters.

At 870, the first and second quantitative attributes can be evaluated, such as to discern a trend. In an example, the first and second quantitative attributes can indicate the total areas of the first and second functions, respectively. The evaluation can indicate that the total area decreased from the first time window to the second time window. In an example, the first time window can indicate thoracic impedance measurements for a patient taken during a first week, and the second time window can indicate thoracic impedance measurements taken during a subsequent week. The evaluation of the first and second quantitative attributes of total area can, in an example, indicate a decreasing area trend. Additional quantitative attributes can be evaluated to identify a trend over a longer period of time, such as several weeks or months. A trend, such as decreasing total area, can indicate a patient health status or risk factor.

At 880, a heart failure decompensation indicator can be provided using the trend. In an example, the total area defined by the first and second functions can indicate a decreasing trend. Decreasing total area can indicate an increased patient risk for heart failure decompensation. An alert can be provided to the patient or clinician after detecting an increased patient risk, such as using telemetry circuitry in the CRM 102, communicatively coupled with an external patient management device.

Turning now to posture detection, patient posture can affect the thoracic impedance of a patient. Sensors, such as including an electrode pair comprising one Can electrode and one or more of the electrodes from the implantable lead system 110, can detect the posture or posture changes of a patient. The electrodes can be located on opposite sides of a patient's thorax, or can be located in cardiac tissue, or a combination of such locations. For example, an electrode can be located near the spine of a patient for delivery of therapy, and an implantable device with an electrode included at its housing 101 can be implanted in a patient's abdomen or chest.

Figure 9:
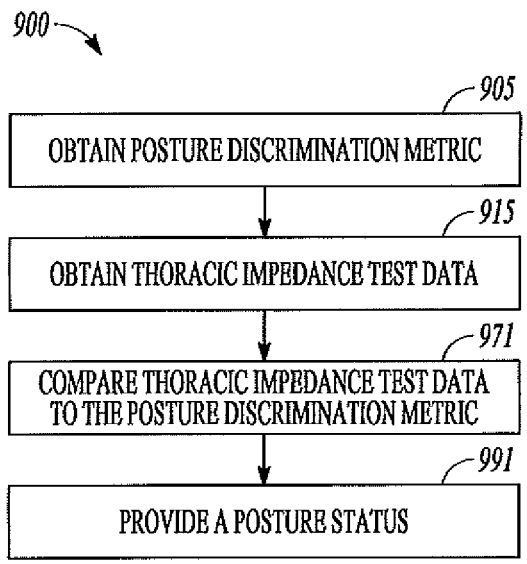
FIG. 9 illustrates generally an example that can include obtaining a posture discrimination metric, obtaining thoracic impedance test data, comparing the thoracic impedance test data to the posture discrimination metric, and providing a posture status.

FIG. 9 illustrates generally an example 900 that can include obtaining a posture discrimination metric 905, obtaining thoracic impedance test data 915, comparing the thoracic impedance test data to the posture discrimination metric 971, and providing a posture status 991.

At 905, a posture discrimination metric can be obtained. In an example, obtaining the posture discrimination metric can include using first thoracic impedance data and second thoracic impedance data. The first thoracic impedance data can be measured using a first electrode configuration defining a first thoracic impedance vector, such as using a combination of electrodes in the implantable lead system 110. The first thoracic impedance data can correspond to one or more instances over a first time window. The second thoracic impedance data can be measured using a second electrode configuration defining a second thoracic impedance vector, wherein the second electrode configuration is different than the first electrode configuration. The second thoracic impedance data can correspond to one or more instances over the same first time window.

In an example, quantitative attributes of the first thoracic impedance data and the second thoracic impedance data can be used to form a posture discrimination metric. The average or median or other central tendency of a set of impedance data can be used, such as to establish a threshold impedance. Impedance values exceeding the threshold can correspond to a first posture, and impedance values less than the threshold can correspond to a second posture. In an example, several quantitative attributes can be used to form the posture discrimination metric, such as to improve the specificity of the metric. In addition to using the average or median of a set of impedance data, the magnitude of the modulation of an impedance vector over a given time window can be used, such as to create a more discriminating metric.

In an example, the first thoracic impedance data and the second thoracic impedance data can be used to form a function, such as can be obtained by plotting the first thoracic impedance data against the second thoracic impedance data on rectangular Cartesian coordinates. The function can be discretized into one or more portions of the function to form the posture discrimination metric. For example, a first portion of the function can correspond to a first posture, and a second portion of the function can correspond to a second posture. In an example, a portion of the function can be associated with a data cluster, or several different portions of the function can be associated with several different data clusters.

Data clusters formed using the first thoracic impedance data and the second thoracic impedance data can be used to form the posture discrimination metric. Discrete data clusters can correspond to a plurality of patient postures, and can be used to determine a patient posture, such as by comparing presently acquired physiological information. In an example including two data clusters, a first data cluster can represent a first patient posture, and a second data cluster can represent a second patient posture. An additional data cluster, if available, can represent an intermediate patient posture. Various techniques, such as regression analysis or discriminant analysis, can identify the boundaries of the data clusters.

In an example, obtaining the posture discrimination metric can include a learning or training period. The first and second thoracic impedance data can be monitored, such as over a first time window including one week, to establish a baseline patient impedance data set. The baseline data set can be evaluated for clustering, and a posture can be attributed to a particular cluster. The posture-cluster correlation can be established manually, such as by a clinician, or automatically, such as by processor-driven analysis. In an example, the learning period can be performed in a clinical setting during or after implant of the CRM 102. In an example, the learning period can include the use of a posture sensor or accelerometer.

In an example, time of day information can be used at least in part to determine the posture comparison metric. Changes in patient posture can generally be expected at regular, periodic intervals, such as including when a patient will lie down in the evening or rise in the morning. Thus, when an accumulation of thoracic impedance data is evaluated to establish the posture comparison metric, the processor or clinician can review relatively narrow time windows where a posture change is likely to have occurred. In an example, a patient can record sleep/wake times during a first time window for subsequent correlation to impedance data acquired during the same first time window.

At 915, thoracic impedance test data can be obtained. The thoracic impedance test data can be obtained using a variety of hardware components including the implantable lead system 110, a subcutaneous electrode array, or an array of electrodes located on a body surface. In an example, at least two electrodes are used to define a test impedance vector used to obtain the thoracic impedance test data. In an example, obtaining the thoracic impedance test data can include using the same implantable lead system 110 or same portion of the same implantable lead system 110 as can be used during the learning or training period. A vector configuration used for obtaining the thoracic impedance test data at 915 can be substantially the same as a vector configuration used during the learning or training period.

At 971, thoracic impedance test data can be compared to the posture discrimination metric. The comparison of the impedance test data to the posture discrimination metric can be performed using the processor circuit 108. The comparison can also be performed manually, such as by a clinician evaluating patient data. In an example, thoracic impedance test data can be obtained using one test impedance vector, and can be compared to one or more posture comparison metrics obtained at 905. In an example where the posture comparison metric includes an average of the first thoracic impedance data and the second thoracic impedance data, the thoracic impedance test data can be compared to the average.

In an example, the thoracic impedance test data can include data from a first test impedance vector and a second test impedance vector. The first thoracic impedance vector can be the same as the first test impedance vector, and the second thoracic impedance vector can be the same as the second test impedance vector. Where data from the first thoracic impedance vector and the second thoracic impedance vector are used to form a function, including at least two data clusters, the data from the first and second test impedance vectors can be compared to the function. Referring now to FIG. 5A, the data from the first and second test impedance vectors can include, during a first time window, an RA-Can impedance measurement of 40 ohms, and an RV-Can impedance measurement of 36 ohms. During a second time window, an RA-Can impedance measurement can be 40 ohms, and an RV-Can impedance measurement can be 33 ohms. The data from the first and second test impedance vectors can be compared to the data clusters 541, 542.

At 991, a posture status can be provided. In an example, the result of the comparison of the thoracic impedance test data and the posture discrimination metric can be used to provide the posture status. In an example, the posture discrimination metric can include a threshold value. A comparison of the test impedance data to the threshold value can determine a patient posture if an appropriate quantitative attribute of the test impedance data meets or exceeds the threshold value.

In an example including the clustering of first and second thoracic impedance data, posture status can be provided by identifying one or more clusters associated with the thoracic impedance test data. For example, the data point 443 in FIG. 4A falls within the upper cluster 441. Where the upper cluster is associated with a recumbent patient posture, the data point 443 can correspond to a recumbent patient posture as well. Thus, it can be determined that the patient was in a recumbent posture during at least a portion of the first time window when the test impedance data was acquired.

The data point 444 in FIG. 4A falls outside of the data clusters 441 and 442. However, the data point 444 can be evaluated for association with one or more of the data clusters 441 and 442. In an example, the data clusters 441 and 442 can correspond to impedance data acquired, such as using the RA-Can impedance vector 331 and the RV-Can impedance vector 332, at multiple instances during a first time window. Data point 444 can correspond to test thoracic impedance data acquired using the RA-Can impedance vector 331 and the RV-Can impedance vector 332 during a second time window. A first belonging-factor can be calculated using the data point 444 and the upper cluster 441, and a second belonging-factor can be calculated using the data point 444 and the lower data cluster 442. The data point 444 can be associated with one of the data clusters 441, 442 using a comparison of the first and second belonging-factors. For example, the belonging-factor can include distance from the data point 444 to the centroids of each of the data clusters 441 and 442. In the example of FIG. 4A, the distance from the data point 444 to the centroid of the lower cluster 442 is less than the distance from the data point 444 to the centroid of the upper cluster 441. Thus, the data point 444 can be associated with the lower cluster 442. This association can indicate that the patient was in an upright position during at least a portion of the second time window. In an example, the belonging-factor can include a probability associated with a data point, such as to provide the probability that a data point is associated with a known posture or data cluster.

Figure 10:
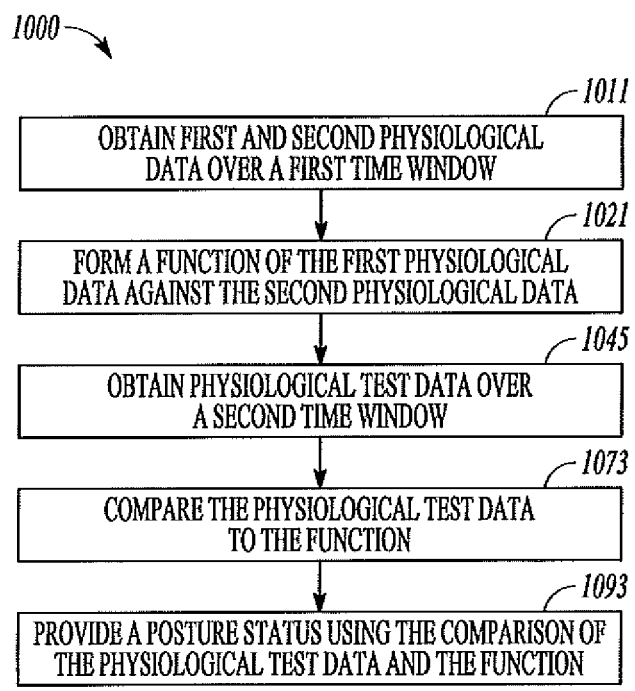
FIG. 10 illustrates generally an example that can include forming a function of first physiological data against second physiological data and providing a posture status using the comparison of physiological test data and the function.

FIG. 10 illustrates generally an example 1000 that can include obtaining first and second physiological data over a first time window 1011, forming a function of the first physiological data against the second physiological data 1021, obtaining physiological test data over a second time window 1045, comparing the physiological test data to the function 1073, and providing a posture status using the comparison of the physiological test data and the function 1093.

At 1011, first and second physiological data can be obtained over a first time window, such as described above in the discussion of FIG. 8 at 810. The first and second physiological data can be obtained using a plurality of different physiological sensors. The first time window can be any duration that permits sufficiently accurate acquisition of the first and second physiological data using the plurality of physiological sensors. The necessary time to obtain the data will vary according to the type of sensor used.

At 1021, a function can be formed using the first and second physiological data. The function can be formed according to the discussion of FIG. 7 at 720. In an example, the function can indicate one or more of a baseline patient pathological state, a current patient physiological state, or it can identify one or more physiological trends using the first and second physiological data. A baseline patient physiological state can provide information that can be monitored or tracked relative to a patient's physiological signals, such as using the processor circuit 108. The baseline can be established by the manufacturer of a medical device, or the baseline can be established by a clinician, such as before, during, or after a device implantation procedure. In an example, the baseline can be established as a rolling average of recent patient information, such as first and second physiological data, or a series of quantitative attributes associated with a function of the first and second physiological data. Evaluation criteria can also be established to provide an index or metric for comparison to the baseline. For example, the baseline can be used for comparison with test data to provide a patient posture status. Because the baseline can be a rolling average, it can change with time. A changing baseline can be monitored, such as using the processor circuit 108 to monitor the deviation of the baseline from a previous or pre-set value, to ensure that physiological information is accurately evaluated.

At 1045, physiological test data can be obtained over a second time window. The physiological test data can be obtained in the same manner as the first and second physiological data, and the physiological test data can correspond to a second time window that can be different than the interval used to obtain the first and second physiological data. In an example, the physiological test data can be obtained using the same physiological sensor as is used to obtain one or more of the first or second physiological data, such as an accelerometer or impedance sensor. The second and fourth physiological data can be obtained using the same physiological sensor, such as an implantable pressure sensor located in the thorax of a patient. In an example, the second time window can be a different duration than the first time window.

At 1073, the physiological test data can be compared to the function. The comparison of the physiological test data and the function can be performed by the processor circuit 108 or an external data receiving and processing circuit. The comparison can also be performed manually, such as by a clinician.

In an example, the physiological test data can include any parameter or characteristic determinable or measurable from the patient's physiological information, such as including data from a first test impedance vector and a second test impedance vector. The first physiological sensor can be the same as the first test impedance vector, and the second physiological sensor can be the same as the second test impedance vector. Where data from the first physiological sensor and the second physiological sensor are used to form a function, including at least two data clusters, the data from the first and second test impedance vectors can be compared to the function. In an example, a quantitative attribute of the data from the first and second test impedance vectors can be compared to a quantitative attribute of the function or data clusters. Referring now to FIG. 5A, the data from the first and second test impedance vectors can include, during a first time window, an RA-Can impedance measurement of 40 ohms, and an RV-Can impedance measurement of 36 ohms. During a second time window, an RA-Can impedance measurement can be 40 ohms, and an RV-Can impedance measurement can be 33 ohms. The data from the first and second test impedance vectors can be compared to the data clusters 541, 542.

At 1093, a posture status can be provided using the comparison of the physiological test data and the function. In an example including the clustering of first and second physiological sensor data, a patient posture status, corresponding to at least a portion of the first time window, can be provided by identifying one or more clusters associated with the physiological test data. For example, the data point 543 in FIG. 5A falls within the upper cluster 541. The data point 543 thus corresponds to the same patient posture associated with the upper cluster 541, such as a recumbent patient posture.

The data point 544 in FIG. 5A falls outside of the data clusters 541 and 542. However, the data point 544 can be evaluated for association with one or more of the data clusters 541 and 542. For example, the distance between the data point 544 and the nearest data point associated with a cluster can be calculated. The data point 544 can be associated with the data cluster including the nearest data point. In this example, the data point 544 can be associated with the lower cluster 542, and can be used to indicate a patient posture.

Figure 11:
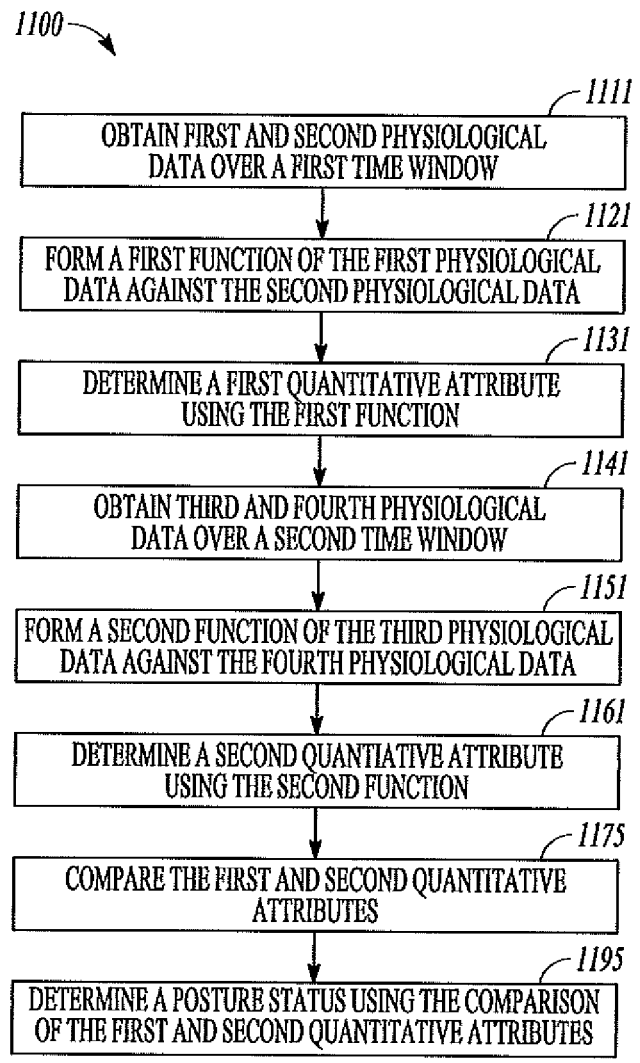
FIG. 11 illustrates generally an example that can include determining a first quantitative attribute using a first function of first physiological data against second physiological data, determining a second quantitative attribute using a second function of third physiological data against fourth physiological data, and determining a posture status using a comparison of the first and second quantitative attributes.

FIG. 11 illustrates generally an example 1100 that can include obtaining first and second physiological data over a first time window 1111, forming a first function of the first physiological data against the second physiological data 1121, determining a first quantitative attribute using the first function 1131, obtaining third and fourth physiological data over a second time window 1141, forming a second function of the third physiological data against the fourth physiological data 1151, determining a second quantitative attribute using the second function 1161, comparing the first and second quantitative attributes 1175, and determining a posture status using the comparison of the first and second quantitative attributes 1195.

At 1111, first and second physiological data can be obtained over a first time window, such as described above in the discussion of FIG. 8 at 810. The first and second physiological data can be obtained using first and second physiological sensors, respectively, wherein the first and second physiological sensors are different. The first time window can be any duration sufficient to obtain accurate first and second physiological data.

At 1121, a first function of the first physiological data can be formed against the second physiological data. The first function can be formed according to the discussion of FIG. 7 at 720.

At 1131, a first quantitative attribute can be determined using the first function. The first quantitative attribute can include any attribute of the first function, such as the area, volume, or location of a data cluster, among other attributes. The first quantitative attribute can be derived from one or more data clusters formed using one or more portions of the function. For example, the function can describe two data clusters. A first quantitative attribute can include the spread of the two data clusters.

In an example, one or more of the steps 1111, 1121, or 1131 can comprise a learning period of the method to determine a posture status. The learning period can include determining a posture discrimination comparison metric using the first and second physiological data, the first function, or the first quantitative attribute.

At 1141, third and fourth physiological data can be obtained over a second time window. The third and fourth physiological data can be obtained in the same manner as the first and second physiological data, although the third and fourth physiological data can be obtained during a different time interval, such as a second time window. In an example, the first and third physiological data can be obtained using the same physiological sensor, such as an impedance sensor configured to obtain cardiac impedance vector information. The second and fourth physiological data can be obtained using the same physiological sensor, such as an implantable pressure sensor located in the thorax of a patient. In an example, the second time window can be a different duration than the first time window.

At 1151, a second function can be formed using the third physiological data and the fourth physiological data. The second function can be formed in the same manner as the first function, or as described above in the discussion of FIG. 8 at 820.

At 1161, a second quantitative attribute can be determined using the second function. The second quantitative attribute can include any attribute of the second function, such as including the same attributes described above in the discussion of FIG. 8 at 830.

In an example, one or more of the steps 1141, 1151, or 1161 can comprise a testing period of the method to determine a posture status. The testing period can include obtaining information for comparison with a posture discrimination comparison metric, such as using the third and fourth physiological data, the second function, or the second quantitative attribute.

At 1175, the first and second quantitative attributes can be compared. In an example, the first and second quantitative attributes can include impedance magnitude information, centroid location information, or volume information. In an example, first and second areas can be compared. In an example, two or more quantitative attributes can be compared, such as to form a trend. For example, first, second, and third centroid locations, such as associated with first, second, and third time windows, can be evaluated to determine a trend in centroid location. A fourth centroid location, such as corresponding to test thoracic impedance data, can be evaluated for association with the trend.

In an example, intervals associated with quantitative attributes can be used to form a look-up table. Physiological test data can be obtained and compared to the look-up table, such as to provide a posture status. In an example, the first, second, and third centroid locations discussed above can each be associated with a discrete patient posture, or discrete portion of a look-up table. The fourth centroid location can be evaluated for a best fit within the look-up table.

At 1195, a posture status can be determined using the comparison of the first and second quantitative attributes. In an example, the area of a data cluster associated with the first time window can be compared to the area of a data cluster associated with the second time window. A patient posture can be indicated for data points included in overlapping areas.

Additional Notes

Example 1 includes subject matter, such as a medical device, comprising a processor, including a first data input, configured to receive first thoracic impedance data measured using a first electrode configuration defining a first thoracic impedance vector, the first thoracic impedance data corresponding to multiple instances over a first time window, and a second data input, configured to receive second thoracic impedance data measured using a different second electrode configuration defining a second thoracic impedance vector, the second thoracic impedance data corresponding to multiple instances over the same first time window. Example 1 can include subject matter such as a processor-readable medium, including instructions that, when performed by the processor, configure the medical device to: form a posture discrimination comparison metric using the first thoracic impedance data and the second thoracic impedance data, obtain third thoracic impedance data using at least one of the first data input or second data input, and provide a posture status using the third thoracic impedance data and the posture discrimination comparison metric.

In Example 2, the subject matter of Example 1 can optionally include a processor-readable medium including instructions that, when performed by the processor, configure the medical device to: form a first function of the first thoracic impedance data against the second thoracic impedance data, determine a quantitative attribute of the first function, and provide the posture status using the quantitative attribute.

In Example 3, the subject matter of one or any combination of Examples 1-2 can optionally include a processor-readable medium including instructions that, when performed by the processor, configure the medical device to determine a quantitative attribute of the first function, the quantitative attribute including at least one of: a spread of a portion of the first function, a range of a portion of the first function, an area defined at least in part by a portion of the first function, a location or centroid of a portion of the first function, a distance between the locations or centroids of at least two different portions of the first function, or a different second function formed using at least two different portions of the first function.

In Example 4, the subject matter of one or any combination of Examples 1-3 can optionally include the first data input configured to receive third thoracic impedance data measured using the first electrode configuration, the second data input configured to receive fourth thoracic impedance data measured using the second electrode configuration, and a processor-readable medium including instructions that, when performed by the processor, configure the medical device to: form a second function of the third thoracic impedance data against the fourth thoracic impedance data, determine a quantitative attribute of the second function, and provide a posture status using a comparison of a quantitative attribute of the first function and a quantitative attribute of the second function.

In Example 5, the subject matter of one or any combination of Examples 1-4 can optionally include a third data input configured to receive additional physiological data using a physiological sensor, the additional physiological data corresponding to multiple instances over the same first time window, and a processor-readable medium including instructions that, when performed by the processor, configure the medical device to form a multi-dimensional first function using the first thoracic impedance data the second thoracic impedance data, and the additional physiological data.

In Example 6, the subject matter of one or any combination of Examples 1-5 can optionally include a processor-readable medium including instructions that, when performed by the processor, configure the medical device to determine a quantitative attribute including a volume using at least a portion of the multi-dimensional first function.

In Example 7, the subject matter of one or any combination of Examples 1-6 can optionally include a processor-readable medium including instructions that, when performed by the processor, configure the medical device to use posture information to determine the first and second thoracic impedance data used to form the posture discrimination comparison metric.

In Example 8, the subject matter of one or any combination of Examples 1-7 can optionally include a processor-readable medium including instructions that, when performed by the processor, configure the medical device to form a posture discrimination comparison metric including at least two data clusters, each data cluster corresponding to a posture status.

In Example 9, the subject matter of one or any combination of Examples 1-8 can optionally include a processor-readable medium including instructions that, when performed by the processor, configure the medical device to form the posture discrimination comparison metric, including at least two data clusters, using time of day information.

In Example 10, the subject matter of one or any combination of Examples 1-9 can optionally include a processor-readable medium including instructions that, when performed by the processor, configure the medical device to form the posture discrimination comparison metric, including at least two data clusters, using posture information obtained during a learning period.

In Example 11, the subject matter of one or any combination of Examples 1-10 can optionally include the first data input configured to receive the first thoracic impedance data measured using a first electrode located in or near a ventricle of a heart, and at least a different second electrode.

In Example 12, the subject matter of one or any combination of Examples 1-11 can optionally include a processor-readable medium including instructions that, when performed by the processor, configure the medical device to use posture status information to interpret a physiological or pathological status.

In Example 13, the subject matter of one or any combination of Examples 1-12 can optionally include a processor-readable medium including instructions that, when performed by the processor, configure the medical device to provide a posture status using a look-up table to classify a quantitative attribute of the third thoracic impedance data.

Example 14 can include, or can be combined with the subject matter of one or any combination of Examples 1-13 to optionally include subject matter such as a medical device, comprising a processor, including a first data input configured to receive first thoracic impedance data measured using a first electrode configuration defining a first thoracic impedance vector, the first thoracic impedance data corresponding to multiple instances over a first time window including a posture change, and a second data input configured to receive second thoracic impedance data measured using a different second electrode configuration defining a different second thoracic impedance vector, the second thoracic impedance data corresponding to multiple instances over the same first time window. Example 14 can optionally include subject matter such as a processor-readable medium, including instructions that, when performed by the processor, configure the medical device to: form a function of the first thoracic impedance data against the second thoracic impedance data, form a first data cluster using a first portion of the function, the first data cluster associated with a first posture, form a different second data cluster using a second portion of the function, the second data cluster associated with a second posture, obtain test thoracic impedance data using at least two thoracic impedance vectors, and provide a posture status by associating the test thoracic impedance data with one of the first data cluster or the second data cluster.

In Example 15, the subject matter of one or any combination of Examples 1-14 can optionally include a processor-readable medium, including instructions that, when performed by the processor, configure the medical device to obtain the test thoracic impedance data using the first thoracic impedance vector and the second thoracic impedance vector.

In Example 16, the subject matter of one or any combination of Examples 1-15 can optionally include a processor-readable medium, including instructions that, when performed by the processor, configure the medical device to form the different second data cluster using a second portion of the function that is exclusive of the first portion.

In Example 17, the subject matter of one or any combination of Examples 1-16 can optionally include a processor-readable medium, including instructions that, when performed by the processor, configure the medical device to: determine a first belonging-factor using the test thoracic impedance data and the first data cluster, determine a second belonging-factor using the test thoracic impedance data and the different second data cluster, and provide the posture status using the first and second belonging factors.

Example 18 can include, or can be combined with the subject matter of one or any combination of Examples 1-17 to optionally include subject matter such as a system, comprising an implantable medical device, including a first thoracic impedance sensor configured to receive first thoracic impedance data corresponding to multiple instances over a first time window, a second thoracic impedance sensor configured to receive second thoracic impedance data corresponding to multiple instances over the same first time window, and a processor circuit, configured to: receive the first and second thoracic impedance data, receive test thoracic impedance data corresponding to multiple instances over a different second time window, form at least two data clusters using the first and second thoracic impedance data, and determine a posture status using the at least two data clusters and the test thoracic impedance data.

In Example 19, the subject matter of one or any combination of Examples 1-18 can optionally include a storage circuit configured to store a plurality of quantitative attributes.

In Example 20, the subject matter of one or any combination of Examples 1-19 can optionally include a processor circuit, configured to monitor a quantitative attribute of the at least two data clusters over at least the first time window and a subsequent time window.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A medical device, comprising:
a processor, including:
a first data input, configured to receive first thoracic impedance data measured using a first electrode configuration defining a first thoracic impedance vector, the first thoracic impedance data corresponding to multiple instances over a first time window that includes a patient posture change, and wherein the first thoracic impedance data corresponds to multiple patient postures;
a second data input, configured to receive second thoracic impedance data measured using a different second electrode configuration defining a second thoracic impedance vector, the second thoracic impedance data corresponding to multiple instances over the same first time window, and wherein the second thoracic impedance data corresponds to the multiple patient postures; and
a processor-readable medium, including instructions that, when performed by the processor, configure the medical device to:
form a first function of the first thoracic impedance data against the second thoracic impedance data, the first function having multiple output values including information about the multiple patient postures;
identify first and second data clusters using the multiple output values of the first function, wherein each of the first and second data clusters respectively corresponds to a different deemed posture state, and wherein at least one of the first and second data clusters spans an at least two-dimensional space;
form a posture discrimination comparison metric using the first and second data clusters and without prior knowledge of the patient's posture status;
obtain third and fourth thoracic impedance data using the first data input and the second data input, respectively; and
determine a posture status using the third and fourth thoracic impedance data and the posture discrimination comparison metric.

2. The medical device of claim 1, wherein the processor-readable medium includes instructions that, when performed by the processor, configure the medical device to:
determine a quantitative attribute of the first function; and
provide the posture status using the quantitative attribute.

3. The medical device of claim 2, wherein the processor-readable medium includes instructions that, when performed by the processor, configure the medical device to determine the quantitative attribute of the first function, the quantitative attribute including at least one of:
a spread of a portion of the first function;
a range of a portion of the first function;
an area defined at least in part by a portion of the first function;
a location or centroid of a portion of the first function;
a distance between the locations or centroids of at least two different portions of the first function; or
a different second function formed using at least two different portions of the first function.

4. The medical device of claim 2, wherein the first data input is configured to receive the third thoracic impedance data measured using the first electrode configuration;
wherein the second data input is configured to receive the fourth thoracic impedance data measured using the second electrode configuration; and
wherein the processor-readable medium includes instructions that, when performed by the processor, configure the medical device to:
form a second function of the third thoracic impedance data against the fourth thoracic impedance data;

determine a quantitative attribute of the second function; and provide a posture status using a comparison of the quantitative attribute of the first function and the quantitative attribute of the second function.

5. The medical device of claim 2, wherein the processor includes a third data input configured to receive additional physiological data using a physiological sensor, the additional physiological data corresponding to multiple instances over the same first time window; and wherein the processor-readable medium includes instructions that, when performed by the processor, configure the medical device to form a multi-dimensional function using the first thoracic impedance data, the second thoracic impedance data, and the additional physiological data.

6. The medical device of claim 5, wherein the processor-readable medium includes instructions that, when performed by the processor, configure the medical device to determine a quantitative attribute including a volume using at least a portion of the multi-dimensional first function.

7. The medical device of claim 1, wherein the processor-readable medium includes instructions that, when performed by the processor, configure the medical device to use posture information to determine the first and second thoracic impedance data used to form the posture discrimination comparison metric.

8. The medical device of claim 1, wherein the processor-readable medium includes instructions that, when performed by the processor, configure the medical device to form a posture discrimination comparison metric including the first and second data clusters, each data cluster corresponding to a different posture status.

9. The medical device of claim 8, wherein the processor-readable medium includes instructions that, when performed by the processor, configure the medical device to form the posture discrimination comparison metric, including the first and second data clusters, using time of day information.

10. The medical device of claim 8, wherein the processor-readable medium includes instructions that, when performed by the processor, configure the medical device to form the posture discrimination comparison metric, including the first and second data clusters, using posture information obtained during a learning period.

11. The medical device of claim 1, wherein the first data input is configured to receive the first thoracic impedance data measured using a first electrode located in or near a ventricle of a heart, and at least a different second electrode.

12. The medical device of claim 1, wherein the processor-readable medium includes instructions that, when performed by the processor, configure the medical device to use posture status information to interpret a physiological or pathological status.

13. The medical device of claim 1, wherein the processor-readable medium includes instructions that, when performed by the processor, configure the medical device to provide a posture status using a look-up table to classify a quantitative attribute of the third thoracic impedance data.

14. A medical device, comprising:
a processor, including:
a first data input, configured to receive first thoracic impedance data measured using a first electrode configuration defining a first thoracic impedance vector, the first thoracic impedance data corresponding to multiple instances over a first time window including a posture change, and wherein the first thoracic impedance data corresponds to multiple patient postures;

a second data input, configured to receive second thoracic impedance data measured using a different second electrode configuration defining a different second thoracic impedance vector, the second thoracic impedance data corresponding to multiple instances over the same first time window, and wherein the second thoracic impedance data corresponds to the multiple patient postures; and a processor-readable medium, including instructions that, when performed by the processor, configure the medical device to:

form a function of the first thoracic impedance data against the second thoracic impedance data, the function having multiple output values that include information about the multiple patient postures;

form a first data cluster spanning an at least two-dimensional space using a first portion of the multiple output values of the function, the first data cluster deemed to be associated with a first posture, and the first data cluster formed without prior knowledge of the patient's corresponding posture status;

form a different second data cluster spanning an at least two-dimensional space using a second portion of the multiple output values of the function, the second data cluster deemed to be associated with a different second posture, and the second data cluster formed without prior knowledge of the patient's corresponding posture status;

obtain test thoracic impedance data using at least third and fourth thoracic impedance data using the first data input and the second data input, respectively; and determine a posture status by associating the third and fourth thoracic impedance data with one of the first data cluster or the second data cluster.

15. The medical device of claim 14, wherein the processor-readable medium includes instructions that, when performed by the processor, configure the medical device to obtain the third and fourth thoracic impedance data using the first and second thoracic impedance vectors, respectively.

16. The medical device of claim 14, wherein the processor-readable medium includes instructions that, when performed by the processor, configure the medical device to form the different second data cluster using the second portion of the multiple output values of the function, wherein the second portion is exclusive of the first portion.

17. The medical device of claim 14, wherein the processor-readable medium includes instructions that, when performed by the processor, configure the medical device to:

determine a first belonging-factor using the third and fourth thoracic impedance data and the first data cluster;

determine a second belonging-factor using the third and fourth thoracic impedance data and the different second data cluster; and provide the posture status using the first and second belonging factors.

18. A system, comprising an implantable medical device, including:

a first thoracic impedance sensor configured to receive first thoracic impedance data corresponding to multiple instances over a first time window and including a patient posture change, wherein the first thoracic impedance data corresponds to multiple patient postures;

a second thoracic impedance sensor configured to receive second thoracic impedance data corresponding to multiple instances over the same first time window, and wherein the second thoracic impedance data corresponds to the multiple patient postures;

a processor circuit, configured to:
receive the first and second thoracic impedance data;
form a function of the first thoracic impedance data against the second thoracic impedance data, the function having multiple output values that include information about the multiple patient postures, wherein the function is formed without prior knowledge of the patient's posture status;
identify at least two data clusters spanning an at least two-dimensional space in the multiple output values of the function, wherein each of the two data clusters corresponds to a different deemed posture state,
receive test thoracic impedance data corresponding to multiple instances over a different second time window, wherein the test thoracic impedance data includes third and fourth thoracic impedance data obtained using the first data input and the second data input, respectively; and
determine a posture status using the at least two data clusters and the test thoracic impedance data.

19. The system of claim 18, wherein the processor circuit is configured to determine the posture status by identifying one of the at least two two-dimensional data clusters with which the test thoracic impedance data corresponds.

20. The system of claim 19, wherein the first thoracic impedance sensor includes first and second electrodes configured for implantation in a patient body; and
wherein the second thoracic impedance sensor includes the same first electrode and a different third electrode configured for implantation in a patient body.

* * * * *